US012766335B2

(12) United States Patent
Duranti

(10) Patent No.: US 12,766,335 B2
(45) Date of Patent: Oct. 20, 2026

(54) NARROW LIGHT DISTRIBUTION APPARATUS, SYSTEM, AND ASSOCIATED METHODS OF USE AND MANUFACTURE

(71) Applicant: Davide Duranti, Albury (GB)

(72) Inventor: Davide Duranti, Albury (GB)

( * ) Notice: Subject to any disclaimer, the term of this patent is extended or adjusted under 35 U.S.C. 154(b) by 0 days.

(21) Appl. No.: 18/793,743

(22) Filed: Aug. 2, 2024

(65) Prior Publication Data

US 2026/0034380 A1 Feb. 5, 2026

(51) Int. Cl.
*A61N 5/06* (2006.01)
*A61B 17/00* (2006.01)
(Continued)

(52) U.S. Cl.
CPC ...... *A61N 5/06* (2013.01); *A61B 2017/00526* (2013.01); *A61B 2018/00178* (2013.01);
(Continued)

(58) Field of Classification Search
CPC ................ A61N 5/06; A61N 2005/005; A61N 2005/0626; A61N 2005/0632;
(Continued)

(56) References Cited

U.S. PATENT DOCUMENTS 3,986,513 A 10/1976 Stuhl
4,444,189 A 4/1984 Seiverd
(Continued)

FOREIGN PATENT DOCUMENTS

CN 2792537 Y 7/2006
CN 203777515 U 8/2014
(Continued)

OTHER PUBLICATIONS

"A Novel Design of Low Cost LED Photo Therapy Equipment", Published at International Journal of Engineering & Technology Research, Published by Sri Logeshwaran R et al., Published Online in [Dec. 2013] https://iaeme.com/MasterAdmin/Journal_uploads/IJETR/VOLUME_1_ISSUE_2/IJETR_01_02_007.pdf.
(Continued)

*Primary Examiner* — Niketa Patel
*Assistant Examiner* — Sebastian X Lukjan
(74) *Attorney, Agent, or Firm* — Legalforce RAPC Worldwide

(57) ABSTRACT

Disclosed is a narrow light distribution apparatus, system, and associated methods of use and manufacture. In one embodiment, an apparatus comprises an encasement comprising a front panel, a back panel, and a siding. An interencasement space within the encasement is formed when the front panel and the back panel are attached to the siding. An inner panel is situated within the interencasement space. A plurality of electrical sockets are arranged on a front side of the inner panel and the electrical sockets of the inner panel are electrically connected to a power source. The apparatus comprises a plurality of housings and each housing is individually attached to one of the plurality of electrical sockets. The apparatus comprises a plurality of light-emitting diodes and each light-emitting diode is at least partially within one individual housing.

19 Claims, 14 Drawing Sheets

(51) Int. Cl.
*A61B 18/00* (2006.01)
*A61N 5/00* (2006.01)

(52) U.S. Cl.
CPC .................. *A61N 2005/005* (2013.01); *A61N 2005/0626* (2013.01); *A61N 2005/0632* (2013.01); *A61N 2005/0642* (2013.01); *A61N 2005/0652* (2013.01); *A61N 2005/0663* (2013.01); *A61N 2005/0664* (2013.01)

(58) Field of Classification Search
CPC .... A61N 2005/0642; A61N 2005/0652; A61N 2005/0663; A61N 2005/0664; A61N 2005/0662; A61B 2017/00526; A61B 2018/00178
See application file for complete search history.

(56) References Cited

U.S. PATENT DOCUMENTS

| | | | | |
|---|---|---|---|---|
| 4,600,009 | A | 7/1986 | Kramer et al. | |
| 4,703,184 | A | 10/1987 | Wolff | |
| 6,626,932 | B2 | 9/2003 | Whitehurst | |
| 6,896,693 | B2 | 5/2005 | Sullivan | |
| 6,955,684 | B2 * | 10/2005 | Savage, Jr. | A61N 5/0618 607/88 |
| 6,991,644 | B2 | 1/2006 | Spooner et al. | |
| 7,131,990 | B2 | 11/2006 | Bansal et al. | |
| 9,044,595 | B2 | 6/2015 | Araya et al. | |
| 9,227,082 | B2 | 1/2016 | McDaniel | |
| 9,399,146 | B2 | 7/2016 | Jones et al. | |
| 9,808,314 | B2 | 11/2017 | Ward | |
| 10,286,225 | B2 | 5/2019 | Baird et al. | |
| 10,363,434 | B2 | 7/2019 | Marchese et al. | |
| 10,525,278 | B2 | 1/2020 | Wasserbauer et al. | |
| 10,828,505 | B2 | 11/2020 | Nelson et al. | |
| 10,912,948 | B2 | 2/2021 | Lin et al. | |
| 11,207,542 | B1 | 12/2021 | Ruzicka | |
| 11,273,320 | B2 | 3/2022 | Woodburn | |
| 11,395,925 | B2 | 7/2022 | Gandel | |
| 11,452,883 | B1 | 9/2022 | Marchese et al. | |
| 2004/0093045 | A1 | 5/2004 | Bolta | |
| 2005/0073839 | A1 | 4/2005 | Pederson et al. | |
| 2006/0229689 | A1 | 10/2006 | Ferguson et al. | |
| 2006/0241726 | A1 | 10/2006 | Whitehurst | |
| 2006/0293727 | A1 | 12/2006 | Spooner et al. | |
| 2007/0129777 | A1 | 6/2007 | Bolta | |
| 2007/0208397 | A1 | 9/2007 | Gardner | |
| 2007/0233209 | A1 | 10/2007 | Whitehurst | |
| 2008/0125835 | A1 * | 5/2008 | Laurent | A61N 5/0617 607/89 |
| 2010/0063487 | A1 | 3/2010 | Van Straalen | |
| 2010/0242155 | A1 * | 9/2010 | Carullo, Jr. | A61N 5/0617 2/171.2 |
| 2015/0112411 | A1 * | 4/2015 | Beckman | A61N 5/0616 607/90 |
| 2015/0134032 | A1 | 5/2015 | Chicchi et al. | |
| 2016/0175608 | A1 | 6/2016 | Livingston | |
| 2016/0367832 | A1 | 12/2016 | Jones et al. | |
| 2018/0236259 | A1 * | 8/2018 | Nelson | A61N 5/0616 |
| 2019/0054310 | A1 | 2/2019 | Woodburn | |
| 2019/0282826 | A1 | 9/2019 | Bellini | |
| 2020/0121944 | A1 | 4/2020 | Strahan et al. | |
| 2020/0176433 | A1 * | 6/2020 | Mueller | H01L 23/5386 |
| 2020/0398075 | A1 | 12/2020 | Pfiffner et al. | |
| 2021/0001141 | A1 | 1/2021 | Pfiffner et al. | |
| 2021/0162231 | A1 | 6/2021 | Ward | |
| 2021/0260402 | A1 | 8/2021 | Moffat, IV | |
| 2021/0290972 | A1 | 9/2021 | Wagenaar Cacciola et al. | |
| 2022/0161049 | A1 | 5/2022 | Gerstenmeier | |
| 2022/0176148 | A1 | 6/2022 | Hetz | |
| 2022/0176150 | A1 | 6/2022 | Gerstenmeier | |
| 2022/0401750 | A1 * | 12/2022 | Daly | A61N 5/0616 |
| 2023/0132952 | A1 | 5/2023 | Youngblood et al. | |
| 2023/0181923 | A1 | 6/2023 | D'Amelio | |
| 2023/0285769 | A1 | 9/2023 | Strahan et al. | |
| 2023/0347164 | A1 | 11/2023 | Lauder et al. | |
| 2023/0414962 | A1 | 12/2023 | Sawyer | |

FOREIGN PATENT DOCUMENTS

| | | | | |
|---|---|---|---|---|
| CN | 216603831 | U | 5/2022 | |
| CN | 217938920 | U | 12/2022 | |
| JP | 2008245836 | A | 10/2008 | |
| KR | 101466447 | B1 | 12/2014 | |
| RU | 221638 | U1 | 11/2023 | |
| WO | WO-2023214999 | A1 * | 11/2023 | A61N 5/06 |

OTHER PUBLICATIONS

"Visible Red Light Emitting Diode Photobiomodulation for Skin Fibrosis: Key Molecular Pathways", Published at Current Dermatology Reports Laser Therapy (J Jagdeo, Section Editor) vol. 5, Published by Andrew Mamalis et al., Published Online on [Apr. 16, 2016] https://link.springer.com/article/10.1007/s13671-016-0141-x.

"Photobiomodulation: Lasers vs Light Emitting Diodes?", Published at Photochemical & Photobiological Sciences, Published by Vladimir Heiskanen et al., Published Online on [Aug. 1, 2018] https://www.ncbi.nlm.nih.gov/pmc/articles/PMC6091542/pdf/nihms-983049.pdf.

"Proposed Mechanisms of Photobiomodulation or Low-Level Light Therapy", Published at IEEE Journal of Selected Topics in Quantum Electronics, Published by Lucas Freitas de Freitas et al., Published Online on [Jun. 9, 2016] https://www.ncbi.nlm.nih.gov/pmc/articles/PMC5215870/pdf/nihms797827.pdf.

"Effects of low-power light therapy on wound healing: LASER x LED", Published at Anais Brasileiros de Dermatologia, Published by Maria Emília de Abreu Chaves et al., Published Online in [Aug. 2014] https://www.ncbi.nlm.nih.gov/pmc/articles/PMC4148276/pdf/abd-89-04-0616.pdf.

"Efficacy of Low-Level Laser Therapy for Body Contouring and Spot Fat Reduction", Published at Obesity Surgery, Published by Mary K. Caruso-Davis et al., Published Online on [Apr. 15, 2010] https://www.ncbi.nlm.nih.gov/pmc/articles/PMC5225499/pdf/nihms-840740.pdf.

"Biological Effects of Low Level Laser Therapy", Published at Journal of Lasers in Medical Sciences, Published by Shirin Farivar et al., Published Online on [Mar. 16, 2014] https://journals.sbmu.ac.ir/jlms/article/view/5540/pdf_8.

"The use of low level laser therapy in the treatment of temporomandibular joint disorders. Review of the literature". Published at Medicina Oral Patologia Oral Cirugia Bucal, Published by Judit Herranz-Aparicio et al., Published Online on [Jul. 1, 2013] http://www.medicinaoral.com/pubmed/medoralv18_14_p603.pdf.

"Low-level laser (light) therapy (LLLT) on muscle tissue: performance, fatigue and repair benefited by the power of light", Published at Photonics & Lasers in Medicine, Published by Cleber Ferraresi et al., Published Online on [Nov. 8, 2012] https://www.degruyter.com/document/doi/10.1515/plm-2012-0032/html.

"Biphasic Dose Response in Low Level Light Therapy", Published at Dose Response, Published by Ying-Ying Huang et al., Published Online on [Sep. 1, 2009] https://www.ncbi.nlm.nih.gov/pmc/articles/PMC2790317/pdf/drp-07-358.pdf.

"Low-Level Laser Therapy for Fat Layer Reduction: A Comprehensive Review", Published at Lasers in Surgery and Medicine, Published by Pinar Avci et al., Published Online on [Jun. 7, 2013] https://onlinelibrary.wiley.com/doi/epdf/10.1002/lsm.22153.

"Low-Level Laser (Light) Therapy (LLLT) for Treatment of Hair Loss", Published at Lasers in Surgery and Medicine, Published by Pinar Avci et al., Published Online on [Aug. 23, 2013] https://onlinelibrary.wiley.com/doi/epdf/10.1002/lsm.22170.

"Is Light-Emitting Diode Phototherapy (LED-LLLT) Really Effective?", Published at Laser Therapy, Published by Won- Serk Kim et al., Published Online on [Sep. 22, 2011] https://www.jstage.jst.go.jp/article/islsm/20/3/20_3_205/_pdf/-char/en.

(56) References Cited

OTHER PUBLICATIONS

"The Nuts and Bolts of Low-level Laser (Light) Therapy", Published at Annals of Biomedical Engineering, Published by Hoon Chung et al., Published Online on [Nov. 2, 2011] https://www.ncbi.nlm.nih.gov/pmc/articles/PMC3288797/pdf/nihms339992.pdf.
"NovoTHOR Whole-body Red Light Therapy", by THOR Photomedicine Ltd., Found Online on [Aug. 20, 2024] https://www.novothor.com/.
"Photobiomodulation (PBM) Therapy Devices for Pain Relief", by Erchonia, Found Online on [Aug. 20, 2024] https://erchonia-emea.com/photobiomodulation-devices/.
"The Effects of Whole-Body Photobiomodulation Light-Bed Therapy on Creatine Kinase and Salivary Interleukin-6 in a Sample of Trained Males: A Randomized, Crossover Study", Published at Frontiers in Sports and Active Living, Published by Jamie J. Ghigiarelli et al., Published Online on [Apr. 29, 2020] https://www.ncbi.nlm.nih.gov/pmc/articles/PMC7739664/pdf/fspor-02-00048.pdf.
"Ultraviolet Light Therapy and Psoriasis—Nursing Perspectives", Published at International Journal of Nursing Education, Published by Padmavathi Nagarajan et al., Published Online on [Jan. 2013] https://www.indianjournals.com/ijor.aspx?target=ijor:ijone&volume=5&issue=1&article=031&type=pdf.
"Phototherapy: A Review of the Literature", Published by Sarah Malerich et al., Found Online on [Dec. 11, 2024] https://cdn.ymaws.com/www.aocd.org/resource/resmgr/jaocd/contents/volume40/40-11.pdf.

* cited by examiner

NARROW LIGHT DISTRIBUTION APPARATUS, SYSTEM, AND ASSOCIATED METHODS OF USE AND MANUFACTURE

FIELD OF TECHNOLOGY

This disclosure relates generally to the field of narrow light distribution systems and associated methods of use and manufacture of the same, and more particularly to a narrow light distribution apparatus and associated methods of use and manufacture, according to one embodiment.

BACKGROUND

A light therapy device may be used to provide targeted light therapy treatment for various medical, therapeutic, cosmetic, and/or wellness applications by shining and/or focusing light onto a user. The light therapy device may face challenges that hinder its effectiveness and/or efficiency.

The light therapy device may lack the precision and/or power necessary to penetrate deeply into the user's tissues which may lead to inadequate stimulation of cellular processes and thus limited and/or nonexistent medical, therapeutic, cosmetic, and/or wellness benefits. The light therapy device may not generate sufficient power to ensure deep tissue penetration, which may prohibit the light therapy device from producing light that activates the mitochondria, which may thus limit optimal cellular energy production and/or inhibition of cortisol stress responses.

The inability to achieve this depth of penetration may result in poor therapeutic outcomes, including but not limited to insufficient stimulation of cellular activities, reduced ATP production, ineffective detoxification processes, and/or suboptimal anti-inflammatory effects. These limitations may lead to inadequate tissue healing, prolonged recovery times, and/or overall diminished effectiveness of the light therapy treatment, thus failing to address the underlying health issues comprehensively.

Moreover, existing light therapy devices may not provide a sufficiently focused light beam. The beam angles of light from these devices may be too wide, leading to scattered and/or diffused light that fails to concentrate energy effectively on the targeted tissues. This lack of focused light may reduce the efficiency of light absorption by tissues, cells, and/or cellular components which may further diminish the user's medical, therapeutic, cosmetic, and/or wellness benefits.

Furthermore, the light therapy device may not effectively target specific wavelengths optimally absorbed by tissues, cells, and/or cellular components, which may limit cellular energy production and/or stress responses. The absence of proper modulation of tissue and/or cellular stress responses and/or enhancement of detoxification pathways may limit the overall effectiveness of the light therapy device. Additionally, the inability to reduce inflammation effectively may prevent optimal tissue function and/or healing.

Last, the light therapy device may struggle to cover large surface areas which may require prolonged exposure times to achieve the desired medical, therapeutic, cosmetic, and/or wellness results, which may be impractical for comprehensive therapy. The light therapy device may not ensure uniform light distribution, resulting in uneven treatment areas and/or inconsistent outcomes. The rigidity and/or lack of adaptability in current systems may fail to address individual patient needs, leading to unpredictable and/or inconsistent therapeutic results.

Therefore, the user may not receive optimal medical, therapeutic, cosmetic, and/or wellness results and/or may be harmed.

SUMMARY

Light distribution devices and methods of use and manufacture of the same are described, and more particularly to a narrow light distribution apparatus, system, and associated methods of use and manufacture.

In one aspect, an apparatus includes an encasement comprising a front panel, a back panel, and a siding. An interencasement space within the encasement is formed when the front panel and the back panel are attached to the siding. An inner panel is situated within the interencasement space. A plurality of electrical sockets are arranged on a front side of the inner panel. The electrical sockets of the inner panel are electrically connected to a power source. The apparatus includes a plurality of housings and each housing is individually attached to one of the plurality of electrical sockets. The apparatus includes a plurality of light-emitting diodes and each light-emitting diode is at least partially within one individual housing. One light-emitting diode is transposed at least partially within one individual housing and the plurality of housings protect the plurality of light-emitting diodes and move power from the electrical sockets to the light-emitting diodes.

The apparatus includes a plurality of refraction means and each refraction means is aligned with one of the plurality of light-emitting diodes to direct light emitted from the light-emitting diodes away from the inner panel. The apparatus includes a plurality of openings cut into the front panel and each opening is aligned with one of the plurality of light-emitting diodes, one of the plurality of refraction means, and one of the plurality of housings. A panel wire electrically connects the power source to the plurality of light-emitting diodes via the plurality of electrical sockets and the plurality of housings. When the power source is delivering power to the plurality of electrical sockets, the light-emitting diodes are powered and emit light through the refraction means and the openings to an area exterior to the apparatus.

The apparatus may include a control panel to control at least one of an on/off switch, light intensity, and/or a timer. The encasement of the apparatus may be substantially cuboid shaped, according to one aspect. The plurality of refraction means may be concave in shape and/or may produce a light beam comprising a beam angle between 25 degrees and 35 degrees when light from the corresponding light-emitting diode passes through it, according to one aspect. Each of the plurality of light-emitting diodes may emit light comprising a wavelength between 600 nanometers and 650 nanometers, according to one aspect.

Each of the plurality of light-emitting diodes may have a wattage between four watts and six watts, according to one aspect. A plurality of fans may be positioned within the interencasement space between a backside of the inner panel and the back panel to cool the apparatus. A plurality of air inlets may be cut into the back panel and each air inlet may be positioned substantially adjacent to at least one of the plurality of fans. The plurality of electrical sockets, the plurality of light-emitting diodes, the plurality of refraction means, and/or the plurality of openings may be arranged in a fifteen unit by forty unit configuration, according to one aspect.

In another aspect, an apparatus includes an encasement comprising a front panel, a back panel, and a siding. An interencasement space within the encasement is formed when the front panel and the back panel are attached to the siding. An inner panel is situated within the interencasement space. A plurality of electrical sockets are arranged on a front side of the inner panel and the front side of the inner panel is adjacent to the front panel of the encasement. The electrical sockets of the inner panel are electrically connected to a power source via a panel wire. The apparatus includes a plurality of housings and each housing is individually attached to one of the plurality of electrical sockets. The plurality of housings are electrically connected to the power source via the electrical sockets and the panel wire.

A plurality of first light-emitting diodes and a plurality of second light-emitting diodes are attached to the inner panel in a checkered pattern. Each first light-emitting diode is at least partially within one individual housing, and each second light-emitting diode is at least partially within one individual housing. The power source is electrically connected to the plurality of first light-emitting diodes and to the plurality of second light-emitting diodes. The panel wire electrically connects the power source to the plurality of first light-emitting diodes and to the plurality of second light-emitting diodes, and when the power source is delivering power to the plurality of electrical sockets, the first light-emitting diodes and the second light-emitting diodes are powered and emit light through a plurality refraction means to an area exterior to the apparatus.

The plurality of refraction means direct and shape the emitted light from the first light-emitting diodes and the second light-emitting diodes away from the inner panel. Each refraction means is aligned with at least one of the plurality of first light-emitting diodes and one of the plurality of second light-emitting diodes. A plurality of openings are cut into the front panel and each opening is aligned with one of the plurality of first light-emitting diodes, one of the plurality of second light-emitting diodes, one of the plurality of refraction means, and one of the plurality of housings.

The apparatus may further include a control panel to control at least one of an on/off switch, light intensity, a timer, and/or light pulsing. The encasement of the apparatus may be substantially cuboid shaped. Each of the plurality of refraction means may be concave in shape and/or produce a light beam comprising a beam angle between 25 degrees and 35 degrees when light from the corresponding light-emitting diode passes through it. Each of the plurality of first light-emitting diodes may emit light comprising a wavelength between 600 nanometers and 650 nanometers. Each of the plurality of second light-emitting diodes may emit light comprising a wavelength between 800 nanometers and 850 nanometers.

Each of the plurality of first light-emitting diodes and/or each of the plurality of second light-emitting diodes may comprise a wattage between four watts and six watts. A plurality of fans may be positioned within the interencasement space adjacent to a backside of the inner panel and/or the back panel of the encasement to cool the components within the interencasement space. A plurality of air inlets may be cut into the back panel and each air inlet may be positioned substantially adjacent to at least one of the plurality of fans. The plurality of electrical sockets, the plurality of refraction means, and/or the plurality of openings may be arranged in a fifteen unit by forty unit configuration.

In yet another aspect a method of manufacturing an apparatus includes constructing an encasement comprising a front panel, a back panel, and a siding by attaching the front panel and the back panel to the siding. When attached to the siding, the front panel, the back panel, and the siding form an interencasement space within the encasement. The method includes securing an inner panel within the interencasement space and the inner panel comprises a plurality of electrical sockets arranged in a specified configuration and electrically connected to a power source. The method includes attaching a plurality of housings to the inner panel and each housing is individually attached to one of the plurality of electrical sockets.

The method includes placing a plurality of light-emitting diodes within the plurality of housings and each light-emitting diode is at least partially within one individual housing. The method includes attaching a plurality of refraction means to the plurality of housings adjacent to the plurality of light-emitting diodes and each refraction means is aligned with one of the plurality of light-emitting diodes to direct and shape the emitted light. The method includes cutting a plurality of openings into the front panel of the encasement and each opening is aligned with at least one light-emitting diode, one refraction means, and one housing. The method includes electrically connecting the power source to the plurality of light-emitting diodes and a panel wire electrically connects the power source to the plurality of light-emitting diodes. The method includes positioning a plurality of fans within the interencasement space adjacent to a backside of the inner panel and the back panel of the encasement to cool the plurality of light-emitting diodes.

The method may include sculpting the plurality of refraction means such that they are concave in shape and emit light at a beam angle in the range of 25 degrees and 35 degrees when light from the corresponding light-emitting diode passes through it. Each of the plurality of light-emitting diodes may have a wattage from four watts and six watts.

In yet another aspect, a method of using a narrow light-emitting apparatus includes positioning the narrow light-emitting apparatus in relation to a user such that a front panel of the narrow light-emitting apparatus is facing the user with a plurality of light-emitting diodes directed at the user. The narrow-light-emitting apparatus comprises an encasement comprising the front panel and a back panel, and when the front panel and the back panel are attached to one another, an interencasement space is formed within the encasement. The narrow-light-emitting apparatus comprises an inner panel situated within the interencasement space and the inner panel comprises a plurality of electrical sockets arranged in a grid configuration on a front side of the inner panel. The electrical sockets of the inner panel are electrically connected to a power source.

The narrow-light-emitting apparatus comprises a plurality of housings and each housing is individually attached to one of the plurality of electrical sockets. Each light-emitting diode is at least partially within one individual housing and the plurality of light-emitting diodes comprises a wattage in a range of four watts to six watts. The narrow-light-emitting apparatus comprises a plurality of refraction means and each refraction means is aligned with one of the plurality of light-emitting diodes to direct and shape light emitted from the light-emitting diodes. The narrow-light-emitting apparatus comprises a plurality of openings cut into the front panel and each opening is aligned with at least one light-emitting diode, one refraction means, and one housing.

The narrow-light-emitting apparatus comprises a panel wire to electrically connect the power source to the plurality of light-emitting diodes via the plurality of electrical sockets and the plurality of housings. When the power source is delivering power to the plurality of electrical sockets, the light-emitting diodes are powered and emit light through the refraction means and the openings to an area exterior to the apparatus. The plurality of refraction means are adjacent to the plurality of light-emitting diodes. Each refraction means is aligned with one of the plurality of light-emitting diodes to direct and shape light emitted from the light-emitting diodes.

The method includes activating the power source to deliver power to the plurality of electrical sockets and thus to the plurality of light-emitting diodes, emitting light from the plurality of light-emitting diodes when the power source delivers power, directing and shaping the emitted light from the plurality of light-emitting diodes through the plurality of refraction means toward the user, and projecting the shaped light through the plurality of openings in the front panel to illuminate the user.

The method may include timing the plurality of light-emitting diodes to project light at the user for a period of five minutes to ten minutes and delivering a fluence of 5 to 10 joules per square centimeter to a tissue of the user, according to one embodiment. Each of the plurality of refraction means may be concave in shape and may produce a light beam comprising a beam angle between 25 degrees and 35 degrees when light from the corresponding light-emitting diode passes through it. Each of the plurality of light-emitting diodes may emit light comprising a wavelength between 600 nanometers and 650 nanometers. Each of the plurality of light-emitting diodes may emit light comprising the wavelength between 800 nanometers and 850 nanometers. The narrow light distribution apparatus may be positioned at a distance of six inches and eight inches away from the user.

Other features will be apparent from the accompanying drawings and from the detailed description that follows.

BRIEF DESCRIPTION OF THE DRAWINGS

The embodiments of this invention are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

Figure 1:
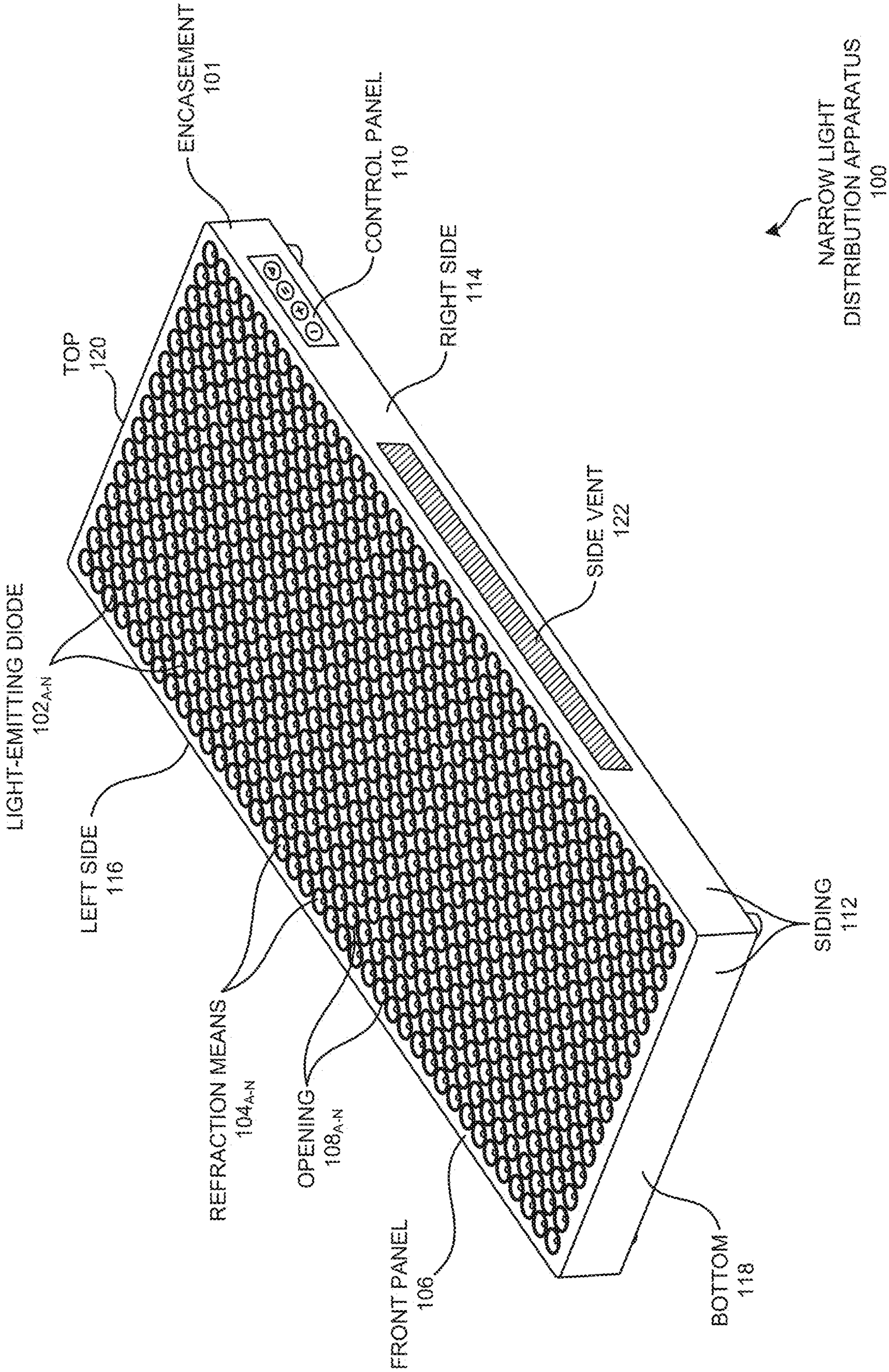
FIG. 1 is a front bottom right side perspective view of the narrow light distribution apparatus, according to one embodiment.

FIG. 1 is a front bottom right side perspective view of the narrow light distribution apparatus 100, according to one embodiment. FIG. 1 illustrates a narrow light distribution apparatus 100 comprising an encasement 101, a plurality of light-emitting diodes 102A-N, a plurality of refraction means 104A-N, a front panel 106 a plurality of openings 108A-N, a control panel 110, a siding 112, a right side 114, a left side 116, a bottom 118, a top 120, and a side vent 122.

The narrow light distribution apparatus 100 may be a device designed to emit focused beams of light for therapeutic and/or other specialized applications. The narrow light distribution apparatus 100 may comprise the encasement 101, internal components, and/or various electronic elements. The narrow light distribution apparatus 100 may provide controlled and/or directed light exposure, which may be used for various tasks including but not limited to medical treatments, industrial processes, and/or other scenarios where precise light distribution is necessary. The narrow light distribution apparatus 100 may include features including but not limited to cooling mechanisms, control interfaces, and/or power management systems to ensure optimal performance and user safety.

The encasement 101 may be the outer structural component of the narrow light distribution apparatus 100. The encasement 101 may be constructed from durable materials including but not limited to metal, plastic, and/or fiberglass. The encasement 101 may comprise the front panel 106, a back panel 200, and/or the siding 112 which may together form an interencasement space 500. The shape of the encasement 101 may be substantially cuboid, but variations may accommodate specific design needs. The encasement 101 may be designed to house internal components including but not limited to the inner panel 300 (not shown) and/or fans 202A-N (not shown). The encasement 101 may include features including but not limited to mounting points, air inlets 204A-N (not shown), and/or the control panel 110.

The plurality of light-emitting diodes 102A-N may be semiconductor devices that convert electrical energy into light. The plurality of light-emitting diodes 102A-N may emit light in specific wavelengths ranging from 600 nanometers to 650 nanometers. The plurality of light-emitting diodes 102A-N may be arranged in a grid configuration and/or specific pattern to ensure uniform light distribution across the target area. The plurality of light-emitting diodes 102A-N may be distributed randomly. Each light-emitting diode 102A-N may also include a heat sink to dissipate heat generated during operation which may ensure stable performance and/or prevent overheating. The plurality of light-emitting diodes 102A-N may include, but are not limited to, Surface-Mounted Device (SMD) LEDs, Chip-on-Board (COB) LEDs, Organic LEDs (OLEDs), Quantum Dot LEDs (QLEDs), Micro LEDs, Infrared LEDs (IR LEDs), and Ultraviolet LEDs (UV LEDs).

The plurality of refraction means 104A-N may be optical components that direct and/or shape the emitted light from the plurality of light-emitting diodes 102A-N. The plurality of refraction means 104A-N may be made from transparent materials including but not limited to glass, silicon, and/or plastic. The plurality of refraction means 104A-N may comprise a substantially concave shape to produce light beams at beam angles between 25 degrees and 35 degrees. The plurality of refraction means 104A-N may be chosen for its optical clarity and/or resistance to heat and/or UV degradation which may ensure that the refraction means 104A-N maintain their shape and/or functional ability over time.

Each of the plurality of light-emitting diodes 102A-N may have a wattage between four watts and/or six watts. The wattage of each light-emitting diode 102A-N may refer to the rate at which electrical energy is consumed by the light-emitting diode 102A-N to produce light. Higher wattage may indicate higher energy consumption, which may correlate with brighter light output, depending on the efficiency of the light-emitting diode 102A-N. The power consumed by the light-emitting diodes 102A-N may also result in heat generation, necessitating the inclusion of heat sinks to manage and dissipate this heat which may ensure stable performance and longevity.

The wavelength of the light emitted by the plurality of light-emitting diodes 102A-N may be between 600 nanometers and 650 nanometers. The wavelength of the light emitted by the plurality of light-emitting diodes 102A-N may be determined by the semiconductor materials and construction of the light-emitting diodes 102A-N and may not be directly influenced by the wattage. The semiconductor materials may include compounds such as gallium arsenide phosphide (GaAsP) or aluminum gallium indium phosphide (AlGaInP), which may be used to produce red, orange, and yellow light. The specific wavelength within the 600 nanometer to 650 nanometer range may be achieved by varying the composition and structure of these semiconductor materials. The construction of the light-emitting diodes 102A-N may involve the layering of these semiconductor materials to create a p-n junction, where electrons and holes recombine to emit light at the desired wavelength. The efficiency and color purity of the emitted light may be enhanced by optimizing the design and fabrication processes of the light-emitting diodes 102A-N.

The refraction means 104A-N may be a substantially circular configuration. Additionally, the plurality of refraction means 104A-N may include, but are not limited to, lenses, prisms, diffraction gratings, holographic optical elements, and/or fiber optic components. Each type of refraction means 104A-N may be selected based on the specific application requirements including but not limited to focusing, beam shaping, and/or spectral dispersion. The refraction means 104A-N may also be designed to optimize light transmission efficiency and/minimize optical aberrations.

Each of the plurality of refraction means 104A-N may be concave in shape and may produce a light beam comprising a beam angle between 25 degrees and/or 35 degrees when light from the corresponding light-emitting diode 102 passes through it. The concave shape of the refraction means 104A-N may bend the light rays inward, causing the light to converge and then diverge at a specific angle, according to one embodiment. As the light-emitting diode 102 emits light, the light beam 1108 may enter the concave surface of the refraction means 104A-N. The curvature of the concave surface may cause the light rays to refract, or bend, towards the central axis of the beam. This bending effect may focus the light rays into a narrower beam as they exit the refraction means 104A-N.

By carefully designing the curvature and material properties of the refraction means 104A-N, the emitted light may be shaped into a beam with a desired angle, according to one embodiment. For instance, a more pronounced concave curvature may result in a tighter beam angle, while a shallower curvature may produce a wider beam angle, according to one embodiment. The materials used for the refraction means 104A-N, which may include glass, silicon, and/or plastic, may also play a role in determining the refractive index, further influencing the beam angle. The combination of these design elements ensures that the light passing through the refraction means 104A-N is directed and/or shaped to create a consistent beam angle between 25 degrees and 35 degrees, optimizing the light distribution for the intended application, according to one embodiment. The refraction means 104A-N may alter the direction and/or distribution of the light but may not change the wavelength of the light, which is determined by the light-emitting diode 102.

The front panel 106 may be a structural component of the encasement 101 of the narrow light distribution apparatus 100. The front panel 106 may be a rectangular shape, a circular shape, an oval shape, a triangular shape, a rectangular shape, and/or any other shape. The front panel 106 may be made from materials including but not limited to metal, fiberglass, silicon, and/or plastic. The front panel 106 may comprise the plurality of openings 108A-N. The front panel 106 may house and/or align the light-emitting diodes 102A-N and/or the refraction means 104A-N with the openings 108A-N. The front panel 106 may also include mounts and/or supports for securing the plurality of light-emitting diodes 102A-N and/or refraction means 104A-N in place. These mounts and/or supports may be designed to provide precise positioning and/or stability which may ensure that the light-emitting diodes 102A-N and/or refraction means 104A-N remain properly aligned during operation.

The front panel 106 may be formed from a single mold process. The front panel 106 may be attached to the siding 112 of the encasement 101 using fastening methods including but not limited to screws, bolts, adhesive bonding, and/or snap-fit mechanisms. This attachment may ensure a secure connection that may maintain the integrity of the encasement 101 and/or provide a stable environment for the internal components. Additionally, the front panel 106 may feature integrated channels and/or pathways to accommodate wiring and/or other connections necessary for the operation of the light-emitting diodes 102A-N and/or refraction means 104A-N. The front panel 106 and/or back panel 200 may attach to the siding 112 to create a secure enclosure and/or interencasement space.

The plurality of openings 108A-N may be apertures cut into the front panel 106 of the encasement 101. The plurality of openings 108A-N may each correspond to an individual light-emitting diode 102 and/or refraction means 104. The plurality of openings 108A-N may be aligned with the plurality of light-emitting diodes 102A-N and/or the plurality of refraction means 104A-N to allow the directed light from the plurality of light-emitting diodes 102A-N and/or the plurality of refraction means 104A-N to be projected outwards to the area exterior to the narrow light distribution apparatus 100. The size, shape, and/or orientation of each of the plurality of openings 108A-N may be tailored to match the size, shape, and/or orientation of each of the refraction means 104A-N and/or the light-emitting diodes 102A-N. This precise alignment may ensure that the emitted light is optimally directed and/or focused through the openings 108A-N.

The structural relationship between the openings 108A-N and the light-emitting diodes 102A-N and/or refraction means 104A-N may be critical for maintaining the efficiency and/or performance of the narrow light distribution apparatus 100, as misalignment may result in reduced light output and/or diminished therapeutic effects. The front panel 106 may incorporate reinforcement features adjacent to the plurality of openings 108A-N to maintain structural integrity and/or prevent deformation under operational stress. Additionally, the positioning and design of the openings 108A-N may facilitate efficient heat dissipation from the light-emitting diodes 102A-N, which may contribute to the overall stability and longevity of the narrow light distribution apparatus 100.

The control panel 110 may be an interface equipped with controls for adjusting the settings of the narrow light distribution apparatus 100, including but not limited to power on/off, light intensity levels, and/or timing functions. The control panel 110 may comprise buttons, switches, and/or touch-sensitive elements. This control panel 110 may include a microcontroller and/or other electronic circuitry to manage the various functions and/or settings of the narrow light distribution apparatus 100. The control panel 110 may be located on the siding 112 of the encasement 101. The control panel 110 may be designed to provide feedback to the user through indicators including but not limited to LED lights, displays, and/or audible signals. The integration of the control panel 110 with the siding 112 may ensure that the internal components are neatly organized and that the wiring and connections to the microcontroller and other electronic circuitry are secure and well-protected. This integration may also help maintain the overall structural integrity and/or aesthetic appearance of the narrow light distribution apparatus 100.

The siding 112 may be the area between the front panel 106 and/or the back panel 200. The siding 112 may form the lateral boundaries of the encasement 101. The siding 112 may be positioned at the outermost edges of the front panel 106 and/or the back panel 200. The siding 112 may comprise the right side 114, the left side 116, the bottom 118, and/or the top 120. The siding 112 may create a contiguous structure around the inner panel 300 (not shown) and/or other internal components. The siding 112 may be formed from a single mold process. Alternatively, the siding 112 may comprise a plurality of separate components attached to one another which may provide flexibility in manufacturing and/or assembly. The siding 112 may have a width that is wider than the inner panel 300 to ensure the inner panel 300 fits properly within the interencasement space 500.

The siding 112 may be comprised of the same material as the front panel 106 and/or the back panel 200. The siding 112 may be securely joined to the front panel 106 and/or the back panel 200 using screws, bolts, adhesive bonding, and/or snap-fit mechanisms. The siding 112, the front panel 106, and/or the back panel 200 may be jointly formed in a single mold process or in a modular assembly process to accommodate different design and/or manufacturing requirements. Additionally, the siding 112 may comprise the side vent 122 which may facilitate airflow and/or cooling within the encasement 101.

The right side 114 may be one of the vertical sides of the siding 112 of the encasement 101. The right side 114 may be made from the same material as the front panel 106, the back panel 200, and/or the rest of the siding 112, which may ensure consistency in material properties and aesthetic appearance. The right side 114 may also include mounting points and/or brackets for securing the narrow light distribution apparatus 100 in place during use, which may provide stability and ease of installation.

The left side 116 may be one of the vertical sides of the siding 112 of the encasement 101. The left side 116 may be made from the same material as the front panel 106, the back panel 200, and/or the rest of the siding 112, which may maintain uniformity in design. The left side 116 may also include mounting points and/or brackets for securing the narrow light distribution apparatus 100 in place during use, which may ensure reliable positioning and support.

The bottom 118 may be the lowermost horizontal portion of the siding 112 of the encasement 101. The bottom 118 may be made from the same material as the front panel 106, the back panel 200, and/or the rest of the siding 112, which may contribute to the overall structural coherence. The bottom 118 may also include mounting points and/or brackets for securing the narrow light distribution apparatus 100 in place during use, which may provide a stable foundation.

The top 120 may be the uppermost horizontal portion of the siding 112 of the encasement 101. The top 120 may be made from the same material as the front panel 106, the back panel 200, and/or the rest of the siding 112, which may ensure a cohesive and robust construction. The top 120 may also include mounting points and/or brackets for securing the narrow light distribution apparatus 100 in place during use, which may facilitate secure attachment and stability.

The side vent 122 may be an opening/openings located on the siding 112 of the encasement 101. The side vent 122 may facilitate airflow into and/or out of the interencasement space 500, which may aid in the cooling of internal components including but not limited to the light-emitting diodes 102A-N, the inner panel 300, and/or other electronic parts and components. This ventilation may be critical for maintaining optimal operating temperatures and ensuring the longevity and performance of the narrow light distribution apparatus 100.

According to one embodiment, FIG. 1 shows a narrow light distribution apparatus 100 comprising an encasement 101. The encasement may comprise a front panel 106, a back panel 200 (not shown), and/or a siding 112. The encasement 101 may be a substantially cuboid shape.

The narrow light distribution apparatus 100 may comprise a plurality of refraction means 104A-N. Each refraction means 104A-N may be aligned with one of the plurality of light-emitting diodes 102A-N to direct light emitted from the light-emitting diodes 102A-N away from the inner panel 300. Each of the plurality of refraction means 104A-N may be concave in shape and may produce a light beam 1108 comprising a beam angle 1112 between 25 degrees and/or 35 degrees when light from the corresponding light-emitting diode 102 passes through it. Each of the plurality of light-emitting diodes 102A-N may emit light comprising a wavelength between 600 nanometers and 650 nanometers. Each of the plurality of light-emitting diodes 102A-N may have a wattage between four watts and/or six watts.

The narrow light distribution apparatus 100 may comprise a plurality of openings 108A-N that may be cut into the front panel 106. Each opening 108 may be aligned with one of the plurality of light-emitting diodes 102A-N, one of the plurality of refraction means 104A-N, and/or one of the plurality of housings 304A-N.

The narrow light distribution apparatus 100 may comprise a control panel 110 to control at least one of an on/off switch, light intensity, and/or a timer.

Figure 2:
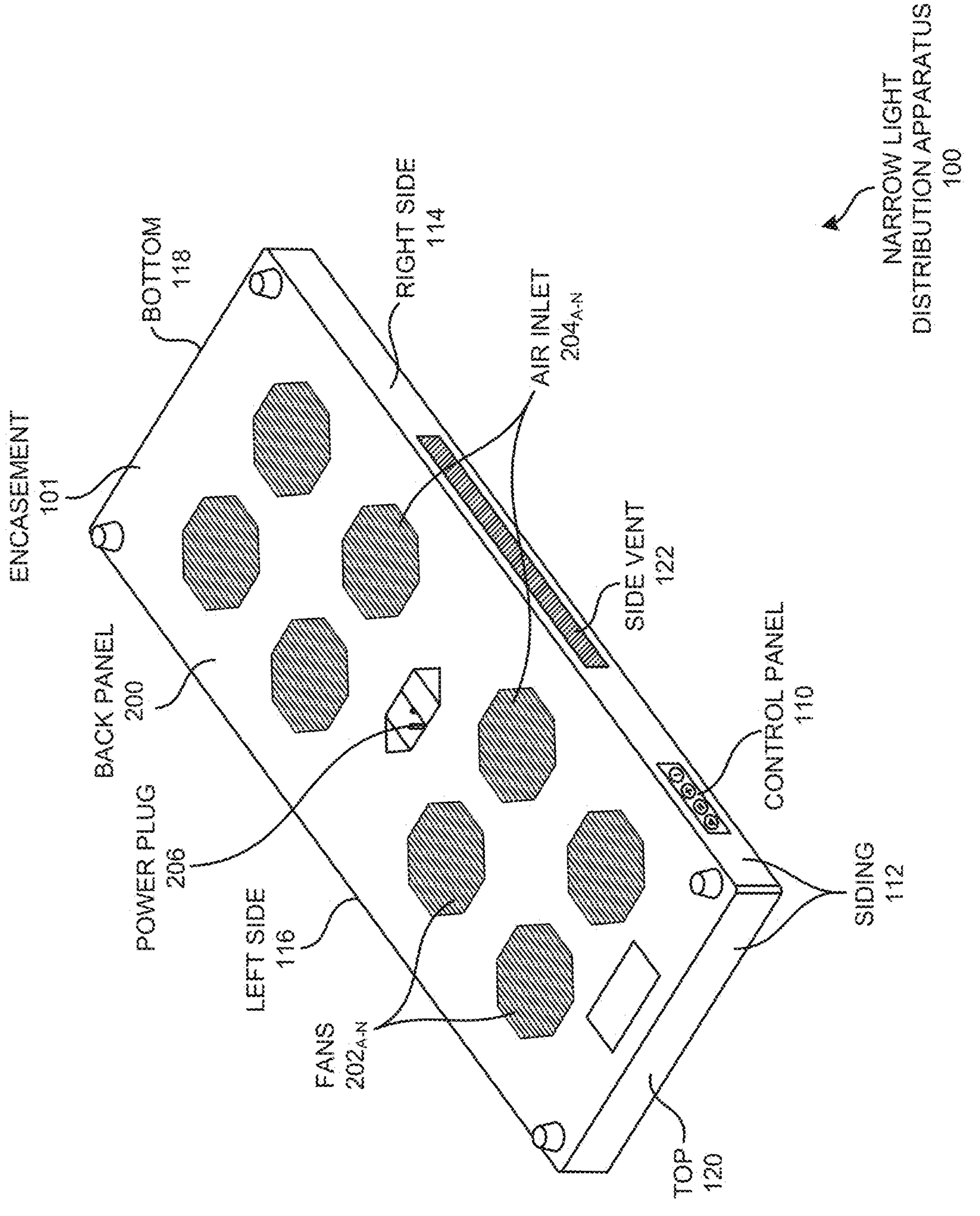
FIG. 2 is a rear top right side perspective view of the narrow light distribution apparatus of FIG. 1, according to one embodiment.

FIG. 2 is a rear top right side perspective view of the narrow light distribution apparatus 100 of FIG. 1, according to one embodiment. FIG. 2 illustrates the narrow light apparatus 100 comprising the encasement 101, the control panel 110, the siding 112, the right side 114, the left side 116, the bottom 118, the top 120, the side vent 122, a back panel 200, a plurality of fans 202A-N, a plurality of air inlets 204A-N, and a power plug 206.

The back panel 200 may be a structural component of the encasement 101. The back panel 200 may be made from materials including but not limited to metal, fiberglass, silicon, and/or plastic. The back panel 200 may comprise a plurality of air inlets 204A-N, which may be openings and/or vents cut into the back panel 200 to allow air to enter and/or flow through the narrow light distribution apparatus 100, aiding in cooling the various components. The back panel 200 may also include a power plug 206, electrical connectors, mounting brackets, and/or additional support structures.

The back panel 200 may connect to the siding 112 of the encasement 101 using fasteners, adhesives, and/or interlocking mechanisms. The connection points may be designed to provide a secure and/or stable attachment, ensuring the structural integrity of the encasement 101. The back panel 200 may be attached to the siding 112 by aligning the edges of the back panel 200 with the corresponding edges of the siding 112 and securing them with screws, bolts, and/or adhesive bonding. This connection method may ensure that the back panel 200 is firmly held in place, providing support for the internal components and maintaining the overall shape and functionality of the narrow light distribution apparatus 100.

In some embodiments, the back panel 200, the siding 112, and the front panel 108 of the encasement 101 may be formed in a single mold process. This integrated molding process may use materials such as plastic or fiberglass to create a single, seamless unit, enhancing the structural integrity and/or reducing the need for additional fasteners or adhesives. The single mold process may ensure precise alignment and fitting of all components, resulting in a robust and aesthetically pleasing encasement 101.

The plurality of fans 202A-N may be cooling devices installed within the interencasement space 500 of the encasement 101 to dissipate heat generated by the light-emitting diodes 102A-N and/or other electronic components. The fans 202A-N may vary in type, including but not limited to axial fans, which may be designed to move air parallel to the axis of the fan, and/or centrifugal fans, which move air perpendicular to the intake of the fan. These fans 202A-N may be made from materials including but not limited to plastic and/or metal, with blades designed for optimal airflow and minimal noise. The fans 202A-N may be strategically placed to ensure efficient cooling to prevent overheating and/or to maintain the performance and longevity of the narrow light distributor 100.

The plurality of air inlets 204A-N may be openings and/or vents cut into the back panel 200 of the encasement 101 to allow air to enter and/or flow through the narrow light distributor 100 which may aid in cooling the various components of the narrow light distribution apparatus 100. The air inlets 204A-N may be designed with filters to prevent dust and/or debris from entering the interencasement space 500 of the encasement 101 which may ensure clean airflow. The air inlets 204A-N may vary in shape and/or size depending on the cooling requirements of the apparatus, and they may be positioned adjacent to the fans 202A-N to maximize airflow and/or cooling efficiency.

The power plug 206 may be an electrical connector that provides the narrow light distributor 100 with a connection to an external power source. The power plug 206 may be designed to accommodate various types of electrical outlets, including but not limited to standard AC plugs for residential and/or commercial use, or specialized plugs for industrial applications. The power plug 206 may be made from durable materials including but not limited to thermoplastic and/or rubber which may ensure safety and/or longevity. Additionally, the power plug 206 may include features including but not limited to a fuse and/or surge protector to safeguard the narrow light distributor 100 against electrical faults and/or surges.

According to one embodiment, FIG. 2 shows the narrow light distribution apparatus 100 comprising a plurality of fans 202A-N that may be positioned within the interencasement space 500 (not shown) between a backside 502 (not shown) of the inner panel 300 and/or the back panel 200 to cool the narrow light distribution apparatus 100. A plurality of air inlets 204A-N may be cut into the back panel 200. Each air inlet 204 may be positioned substantially adjacent to at least one of the plurality of fans 202A-N. The siding 112 (e.g. the right side 114, the left side 116, the bottom 118 and/or the top 120) may be attached to the back panel 200 of the encasement 101 at the outermost portion of the back panel 200.

The power plug 206 may be integrated into the back panel 200 and may allow the narrow light distribution apparatus to be electronically connected to a power source. Electrical power may move from the power source, through power plug 206, and to the various electrical components of the narrow light distribution apparatus 100 (e.g. the electrical sockets 302A-N, the housings 304A-N, the light-emitting diodes 102A-N, the control panel 110, the fans 202A-N, etc.).

Figure 3:
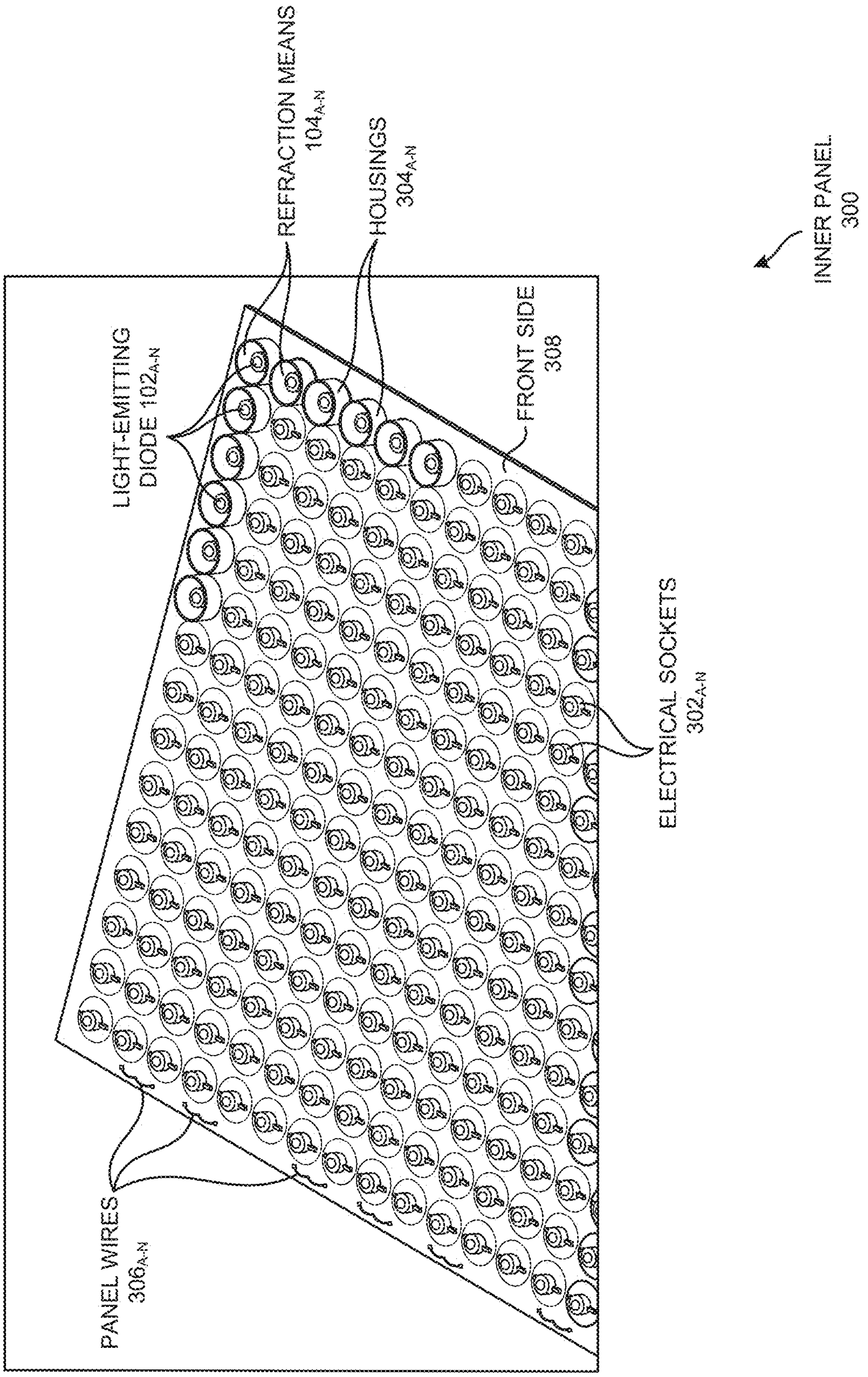
FIG. 3 is a front bottom right side perspective view of the inner panel of the narrow light distribution apparatus of FIGS. 1-2, according to one embodiment

FIG. 3 is a front bottom right side perspective view of the inner panel 300 of the narrow light distribution apparatus 100 of FIGS. 1-2, according to one embodiment. FIG. 3 illustrates the plurality of light-emitting diodes 102A-N, the plurality of refraction means 104A-N, an inner panel 300, a plurality of electrical sockets 302A-N, a plurality of housings 304A-N, one or more panel wire 306A-N, and a front side 308.

The inner panel 300 may be a structural and/or electrical component situated within the interencasement space 500 of the narrow light distribution apparatus 100. The inner panel 300 may comprise the electrical sockets 302A-N, the one or more panel wire 306A-N, the front side 308, and/or a backside 502 (not shown). The inner panel 300 may be made from materials including but not limited to metals (including but not limited to zinc, aluminum, steel, and/or copper), silicon, ceramics, and/or high-strength plastic to provide a sturdy mounting surface for the electrical components and/or a surface with cooling properties.

The inner panel 300 may serve as a central platform to which various electrical and/or optical components are attached including but not limited to the light-emitting diodes 102A-N, housings 304A-N and/or the one or more panel wire 306A-N. The inner panel 300 may be a shape substantially corresponding to the shape of the encasement 101 including but not limited to a rectangle, oval, circle, and/or any other shape. The inner panel 300 may also include integrated pathways and/or channels for the one or more panel wire 306A-N which may allow the one or more panel wire 306A-N to run power to each of the electrical sockets 302A-N.

The plurality of electrical sockets 302A-N may be electrical and/or mechanical connection points for the housings 304A-N. The plurality of electrical sockets 302A-N may be located on the front side 308 of the inner panel 300. The electrical sockets 302A-N may be designed to receive and/or secure the housings 304A-N for the light-emitting diodes 102A-N. The plurality of electrical sockets 302A-N may provide electrical connections to power the light-emitting diodes 102A-N from the power source. The electrical sockets 302A-N may vary in type, including standard sockets, which may provide simple plug-and-play connections, and/or locking sockets, which may offer more secure and/or stable connections to prevent accidental disconnections during operation. The plurality of electrical sockets 302A-N may be made from conductive materials including but not limited to copper and/or brass which may ensure efficient electrical conductivity.

The electrical sockets 302A-N may conform to industry standards, utilizing connectors such as normal American kettle lead plugs, IEC connectors, NEMA connectors, and/or custom-designed connectors, with proper earthing in the center of the inner panel 300. The electrical sockets 302A-N may be housed in insulating materials such as plastic, which may ensure safe and/or reliable electrical connections by preventing electrical shorts and/or protecting the internal components from potential damage. Additionally, the plurality of electrical sockets 302A-N may include features such as polarization to ensure correct orientation during connection, and/or integrated strain relief to prevent damage to the wires and connectors. The electrical sockets 302A-N may be arranged in a specific pattern on the front side 308 of the inner panel 300, such as a grid or staggered configuration, to optimize the layout and ensure uniform light distribution from the light-emitting diodes 102A-N. The design and placement of the electrical sockets 302A-N may facilitate easy maintenance and replacement of individual light-emitting diodes 102A-N and/or housings 304A-N.

The plurality of housings 304A-N may be protective, supportive, and/or conductive structures that electrically connect, mechanically connect, and/or protect the plurality of light-emitting diodes 102A-N. The plurality of housings 304A-N may each be designed to hold an individual light-emitting diode 102A-N. The housings 304A-N may comprise prongs and/or mounts that fit into the electrical sockets 302A-N. These prongs of the housings 304A-N may ensure that the housings 304A-N and/or the light-emitting diodes 102A-N are mounted to the inner panel 300 and/or properly aligned with the refraction means 104A-N and/or openings 108A-N in the front panel 106. The housings 304A-N may be cylindrical, cuboid, or other shapes tailored to specific design requirements which may provide versatility in their application.

The plurality of electrical sockets 302A-N may be arranged in various configurations on the inner panel 300, including but not limited to a grid pattern. The electrical sockets 302A-N, along with the housings 304A-N, light-emitting diodes 102A-N, and refraction means 104A-N, may be configured in patterns such as concentric circles, staggered rows, and/or custom designs tailored to specific light distribution needs. The housings 304A-N may be made from materials including but not limited to metal, plastic, and/or ceramic, which may provide protection against environmental factors and/or help dissipate heat generated by the light-emitting diodes 102A-N.

Additionally, the housings 304A-N may facilitate the transfer of electrical power from the electrical sockets 302A-N to the light-emitting diodes 102A-N. This power transfer may occur through conductive pathways integrated within the housings 304A-N, which may ensure efficient delivery of electricity to the light-emitting diodes 102A-N. The design of the housings 304A-N may also incorporate features to optimize the alignment and stability of the light-emitting diodes 102A-N, enhancing the overall performance and reliability of the narrow light distribution apparatus 100.

The one or more panel wire 306A-N may be an electrical conductor that connects various components within the narrow light distribution apparatus 100. The one or more panel wire 306A-N may be made from materials including but not limited to copper and/or aluminum. The one or more panel wire 306A-N may be insulated with materials including but not limited to PVC and/or silicone to prevent short circuits and/or protect against electrical shocks. The one or more panel wire 306A-N may run from the power source to the electrical sockets 302A-N. The one or more panel wire 306A-N may also be routed through designated pathways in the inner panel 300 to keep the internal layout organized and/or minimize the risk of damage.

The one or more panel wire 306A-N may be attached to the inner panel 300 using various fastening methods including but not limited to clips, clamps, and/or adhesive channels. These attachment methods may secure the one or more panel wire 306A-N in place, preventing movement and reducing the risk of wear and tear due to vibrations or handling, according to one embodiment. The designated pathways in the inner panel 300 may be pre-formed channels or grooves specifically designed to accommodate the one or more panel wire 306A-N, ensuring a neat and orderly arrangement, according to one embodiment.

Additionally, the one or more panel wire 306A-N may be integrated with the inner panel 300 through embedded conduits or molded pathways. These integrated features may provide a streamlined and/or protected route for the one or more panel wire 306A-N, enhancing the durability and reliability of the electrical connections, according to one embodiment. The integration of the one or more panel wire 306A-N with the inner panel 300 may facilitate efficient assembly and/or maintenance of the narrow light distribution apparatus 100 by ensuring that the wiring is systematically organized and/or securely held in place.

The one or more panel wire 306A-N may terminate at the electrical sockets 302A-N, where they may be connected to provide power to the plurality of light-emitting diodes 102A-N. These connections may be made using soldering, crimping, and/or plug-and-socket connectors, ensuring reliable electrical contact and easy assembly or replacement. The overall design of the one or more panel wire 306A-N integration with the inner panel 300 may prioritize safety, case of assembly, and/or long-term reliability.

The front side 308 may be the surface of the inner panel 300 that faces the front panel 106 of the encasement 101. The front side 308 may comprise the electrical sockets 302A-N, which may be integrated directly onto this surface. The front side 308 may ensure that the electrical sockets 302A-N, and thus the housings 304A-N, the light-emitting diodes 102A-N, and/or the refraction means 104A-N, are properly aligned with the openings 108A-N of the front panel 106. The front side 308 may include markings and/or guides to facilitate the precise installation and alignment of the sockets 302A-N and/or housings 304A-N. These markings and/or guides may ensure that the electrical sockets 302A-N, housings 304A-N, light-emitting diodes 102A-N, and/or refraction means 104A-N are correctly positioned for optimal light emission and/or performance. The front side 308 may be treated and/or coated to enhance its durability and/or resistance to environmental factors, which may ensure long-term reliability and performance of the narrow light distribution apparatus 100.

According to one embodiment, FIG. 3 shows the narrow light distribution apparatus 100 comprising an inner panel 300 situated within the interencasement space 500 (not shown). The inner panel 300 of the narrow light distribution apparatus 100 may comprise a plurality of electrical sockets 302A-N that may be arranged on a front side 308 of the inner panel 300. The electrical sockets 302A-N of the inner panel 300 may be electrically connected to a power source.

The inner panel 300 of the narrow light distribution apparatus 100 may further comprise a plurality of housings 304A-N. Each housing 304 may be individually attached to one of the plurality of electrical sockets 302A-N. The narrow light distribution apparatus 100 may further comprise a plurality of light-emitting diodes 102A-N. Each light-emitting diode 102 may be at least partially within one individual housing 304. One light-emitting diode 102 may be transposed at least partially within one individual housing 304, according to one embodiment. The plurality of housings 304A-N may protect the plurality of light-emitting diodes 102A-N and/or move power from the electrical sockets 302A-N to the light-emitting diodes 102A-N.

The inner panel 300 of the narrow light distribution apparatus 100 may comprise one or more panel wire 306A-N to electrically connect the power source to the plurality of light-emitting diodes 102A-N via the plurality of electrical sockets 302A-N and/or the plurality of housings 304A-N. When the power source is delivering power to the plurality of electrical sockets 302A-N, the light-emitting diodes 102A-N may be powered and/or emit light through the refraction means 104A-N and/or the openings 108A-N to an area exterior to the narrow light distribution apparatus 100. Furthermore, the plurality of electrical sockets 302A-N, the plurality of light-emitting diodes 102A-N, the plurality of refraction means 104A-N, and/or the plurality of openings 108A-N may be arranged in a fifteen unit by forty unit configuration (e.g. fifteen corresponding sockets 302A-N, fifteen housings 304A-N, fifteen light-emitting diodes 102A-N, and fifteen refractions means 104A-N wide by forty corresponding sockets 302A-N, forty housings 304A-N, forty light-emitting diodes 102A-N, and forty refractions means 104A-N tall, according to one embodiment).

Figure 4:
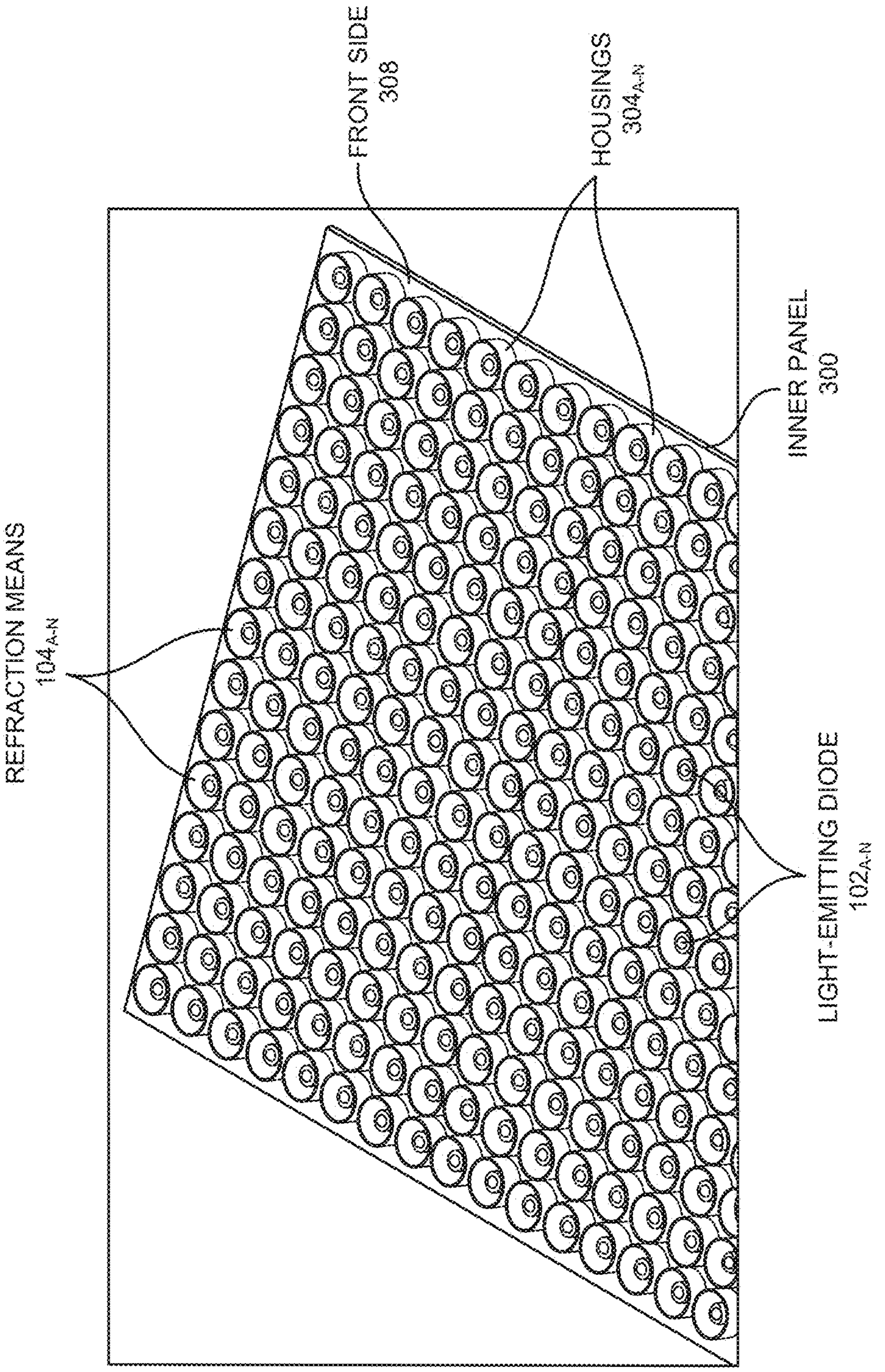
FIG. 4 is a partial view of the inner panel of the narrow light distribution apparatus of FIGS. 1-3, according to one embodiment.

FIG. 4 is a partial view of the inner panel 300 of the narrow light distribution apparatus 100 of FIGS. 1-3, according to one embodiment. FIG. 4 illustrates the plurality of light-emitting diodes 102A-N, the plurality of refraction means 104A-N, the inner panel 300, the plurality of housings 304A-N, and the front side 308.

According to one embodiment, FIG. 4 shows a partial view of the inner panel 300 of the narrow light distribution apparatus 100. The inner panel 300 may comprise a plurality of light-emitting diodes 102A-N, a plurality of refraction means 104A-N, a plurality of housings 304A-N, and a front side 308. The light-emitting diodes 102A-N may be semiconductor devices that convert electrical energy into light. The refraction means 104A-N may be optical components that direct and/or shape the emitted light from the light-emitting diodes 102A-N. The housings 304A-N may be protective, supportive, and/or conductive structures that electrically connect, mechanically connect, and/or protect the light-emitting diodes 102A-N. The front side 308 may be the surface of the inner panel 300 that faces the front panel 106 of the encasement 101. The alignment and arrangement of these components on the inner panel 300 may ensure optimal light emission and/or performance of the narrow light distribution apparatus 100.

Figure 5:
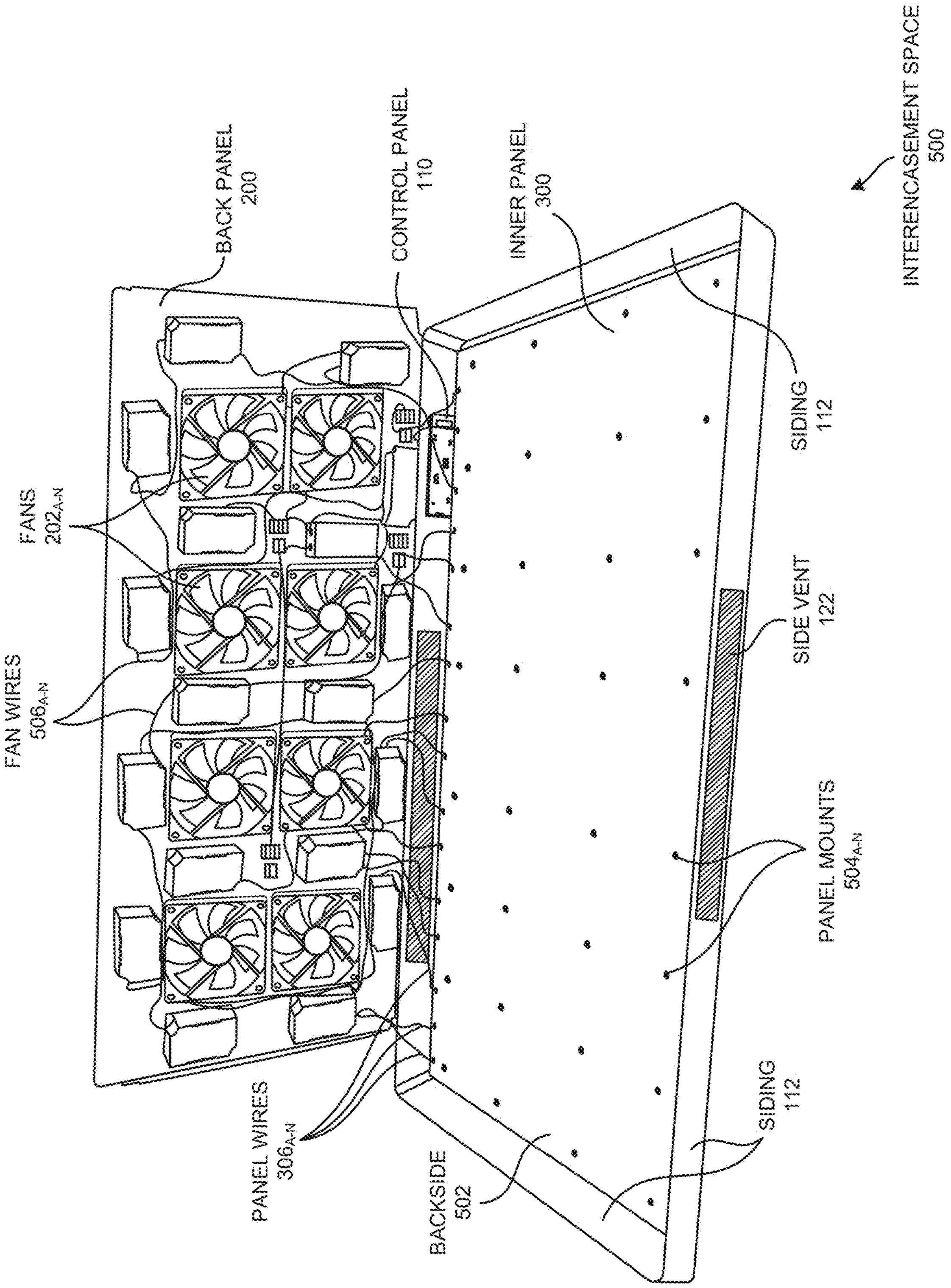
FIG. 5 is a detailed view of the inner components and structure of the narrow light distribution apparatus of FIGS. 1-4, according to one embodiment.

FIG. 5 is a detailed view of the inner components and structure of the narrow light distribution apparatus 100 of FIGS. 1-4, according to one embodiment. FIG. 5 illustrates the narrow light distribution apparatus 100 comprising the control panel 110, the siding 112, the side vent 122, the back panel 200, the fans 202A-N, the inner panel 300, the panel wires 306A-N, an interencasement space 500, a backside 502, a plurality of panel mounts 504A-N, and a plurality of fan wires 506A-N.

The interencasement space 500 may be the internal area formed when the front panel 106 and the back panel 200 are attached to the siding 112. The interencasement space 500 may house various internal components, including but not limited to the inner panel 300, the electrical sockets 302A-N, the housings 304A-N, the one or more panel wire 306A-N, the refraction means 104A-N, the light-emitting diodes 102A-N. the fans 202A-N, the fan wires 506A-N, the panel mounts 504A-N and/or other components. The interencasement space 500 may provide an organized layout for the various components of the narrow light distribution apparatus 100, which may ensure that each element is securely mounted and/or properly aligned. The interencasement space 500 may also facilitate efficient airflow, aided by the plurality of fans 202A-N, which may prevent overheating and/or maintain optimal performance of the light-emitting diodes 102A-N and/or other electronic parts. Additionally, the interencasement space 500 may include pathways for wiring and/or may accommodate various control mechanisms to regulate the operation of the device.

The backside 502 may be the rear surface of the inner panel 300. The backside 502 may support the integration of various components, including but not limited to the electrical sockets 302A-N and/or housings 304A-N. The backside 502 may also include pathways for wiring and/or other connections, which may ensure that electrical and/or mechanical connections remain organized and/or accessible.

The plurality of panel mounts 504A-N may be structural elements used to secure different components within the interencasement space 500. The plurality of panel mounts 504A-N may attach to the inner panel 300 and the back panel 200. The plurality of panel mounts 504A-N may connect other structural parts, which may ensure stability and/or proper alignment of the internal components. The placement and design of the panel mounts 504A-N may facilitate the secure attachment of various elements within the interencasement space 500.

The plurality of fan wires 506A-N may be electrical conductors that connect the fans 202A-N to the power source and/or control panel 110. The plurality of fan wires 506A-N may run through designated pathways in the inner panel 300 and/or other structural elements. The plurality of fan wires 506A-N may provide power and/or control signals to the fans 202A-N, which may ensure efficient cooling of the light-emitting diodes 102A-N and/or other heat-generating components. The routing of the fan wires 506A-N may optimize airflow and/or minimize interference with other components.

According to one embodiment, FIG. 5 shows the narrow light distribution apparatus 100 comprising an interencasement space 500 within the encasement 101 that may be formed when the front panel 106 and/or the back panel 200 are attached to the siding 112. The plurality of fans 202A-N may be positioned within the interencasement space 500 between a backside 502 of the inner panel 300 and/or the back panel 200 to cool the narrow light distribution apparatus 100. The plurality of fans 202A-N may be electrically connected to the power source via a plurality of fan wires 506A-N. The plurality of fans 202A-N may also be communicatively coupled to the control panel 110 (not shown) via the plurality of fan wires 506A-N.

Figure 6:
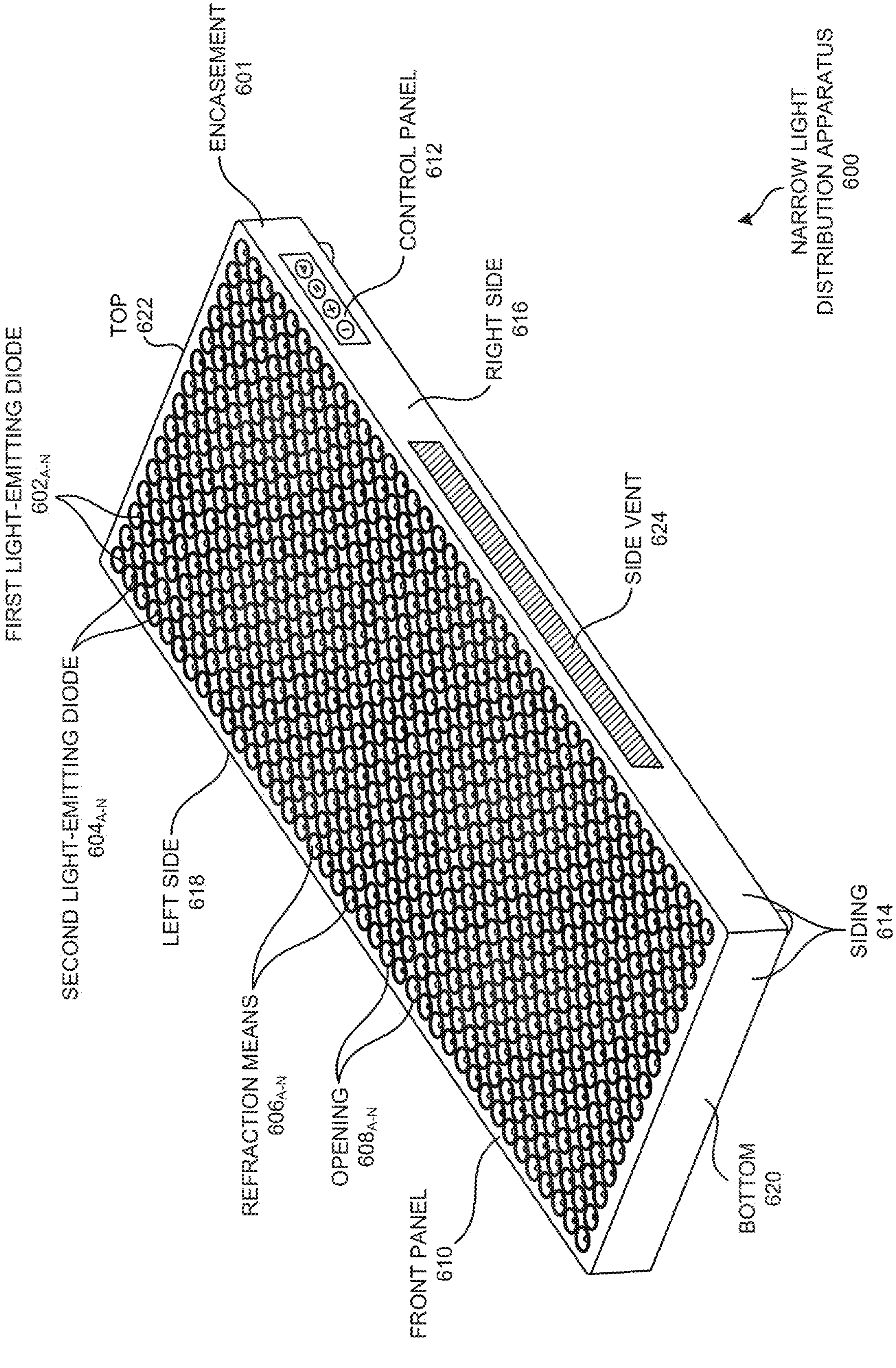
FIG. 6 is a front bottom right side perspective view of an alternative embodiment of the narrow light distribution apparatus of FIGS. 1-5, according to one embodiment.

FIG. 6 is a front bottom right side perspective view of an alternative embodiment of the narrow light distribution apparatus 100 of FIGS. 1-5, according to one embodiment. FIG. 6 illustrates a narrow light distribution apparatus 600 comprising an encasement 601, a plurality of first light-emitting diodes 602A-N, a plurality of second light-emitting diodes 604A-N, a plurality of refraction means 606A-N, a plurality of openings 608A-N, a front panel 610, a control panel 612, a siding 614, a right side 616, a left side 618, a bottom 620, a top 622, and a side vent 624.

The narrow light distribution apparatus 600 may be a device designed to emit focused beams of light for therapeutic and/or other specialized applications. The narrow light distribution apparatus 600 may comprise the encasement 601, internal components, and/or various electronic elements. The narrow light distribution apparatus 600 may provide controlled and/or directed light exposure, which may be used for various tasks including but not limited to medical treatments, industrial processes, and/or other scenarios where precise light distribution is necessary. The narrow light distribution apparatus 600 may include features including but not limited to cooling mechanisms, control interfaces, and/or power management systems to ensure optimal performance and user safety.

The encasement 601 may be the outer structural component of the narrow light distribution apparatus 600. The encasement 601 may be constructed from durable materials including but not limited to metal, plastic, and/or fiberglass. The encasement 601 may comprise the front panel 610, a back panel 200, and/or the siding 614 which may together form an interencasement space 1000. The shape of the encasement 601 may be substantially cuboid, but variations may accommodate specific design needs. The encasement 601 may be designed to house internal components including but not limited to the inner panel 800 (not shown) and/or fans 702A-N (not shown). The encasement 601 may include features including but not limited to mounting points, air inlets 704A-N (not shown), and/or the control panel 612.

The plurality of first light-emitting diodes 602A-N may be semiconductor devices that convert electrical energy into light. The plurality of first light-emitting diodes 602A-N may be arranged in a grid configuration and/or specific pattern to ensure uniform light distribution across the target area. The plurality of first light-emitting diodes 602A-N may be distributed randomly. Each first light-emitting diode 602A-N may also include a heat sink to dissipate heat generated during operation which may ensure stable performance and/or prevent overheating. The plurality of first light-emitting diodes 602A-N may include, but are not limited to, Surface-Mounted Device (SMD) LEDs, Chip-on-Board (COB) LEDs, Organic LEDs (OLEDs), Quantum Dot LEDs (QLEDs), Micro LEDs, Infrared LEDs (IR LEDs), and Ultraviolet LEDs (UV LEDs). The plurality of first light-emitting diodes 602A-N may be electrically connected to a power source. The plurality of first light-emitting diodes 602A-N may be electrically connected to the power source via one or more panel wire 806A-N.

Each of the plurality of first light-emitting diodes 602A-N may have a wattage between four watts and/or six watts. The wattage of each first light-emitting diode 602A-N may refer to the rate at which electrical energy is consumed by the first light-emitting diode 602A-N to produce light. Higher wattage may indicate higher energy consumption, which may correlate with brighter light output, depending on the efficiency of the first light-emitting diode 602A-N. The power consumed by the first light-emitting diodes 602A-N may also result in heat generation, necessitating the inclusion of heat sinks to manage and dissipate this heat which may ensure stable performance and longevity.

The wavelength of the light emitted by the plurality of first light-emitting diodes 602A-N may be between 600 nanometers and 650 nanometers. The wavelength of the light emitted by the plurality of first light-emitting diodes 602A-N may be determined by the semiconductor materials and construction of the first light-emitting diodes 602A-N and may not be directly influenced by the wattage. The semiconductor materials may include compounds such as gallium arsenide phosphide (GaAsP) or aluminum gallium indium phosphide (AlGaInP), which may be used to produce red, orange, and yellow light. The specific wavelength within the 600 nanometer to 650 nanometer range may be achieved by varying the composition and structure of these semiconductor materials. The construction of the first light-emitting diodes 602A-N may involve the layering of these semiconductor materials to create a p-n junction, where electrons and holes recombine to emit light at the desired wavelength. The efficiency and color purity of the emitted light may be enhanced by optimizing the design and fabrication processes of the first light-emitting diodes 602A-N.

The plurality of second light-emitting diodes 604A-N may be semiconductor devices that convert electrical energy into light. The plurality of second light-emitting diodes 604A-N may be arranged in a grid configuration and/or specific pattern to ensure uniform light distribution across the target area, according to one embodiment. The plurality of second light-emitting diodes 604A-N may be distributed randomly. Each second light-emitting diode 604A-N may also include a heat sink to dissipate heat generated during operation which may ensure stable performance and/or prevent overheating. The plurality of second light-emitting diodes 604A-N may include, but are not limited to, Surface-Mounted Device (SMD) LEDs, Chip-on-Board (COB) LEDs, Organic LEDs (OLEDs), Quantum Dot LEDs (QLEDs), Micro LEDs, Infrared LEDs (IR LEDs), and Ultraviolet LEDs (UV LEDs). The plurality of second light-emitting diodes 604A-N may be electrically connected to a power source. The plurality of second light-emitting diodes 604A-N may be electrically connected to the power source via one or more panel wire 806A-N.

Each of the plurality of second light-emitting diodes 604A-N may have a wattage between four watts and/or six watts. The wattage of each second light-emitting diode 604A-N may refer to the rate at which electrical energy is consumed by the second light-emitting diode 604A-N to produce light. Higher wattage may indicate higher energy consumption, which may correlate with brighter light output, depending on the efficiency of the second light-emitting diode 604A-N. The power consumed by the second light-emitting diodes 604A-N may also result in heat generation, necessitating the inclusion of heat sinks to manage and dissipate this heat which may ensure stable performance and longevity.

The wavelength of the light emitted by the plurality of second light-emitting diodes 604A-N may be between 800 nanometers and 850 nanometers. The wavelength of the light emitted by the plurality of second light-emitting diodes 604A-N may be determined by the semiconductor materials and construction of the second light-emitting diodes 604A-N and may not be directly influenced by the wattage. The semiconductor materials may include compounds such as gallium arsenide (GaAs) or aluminum gallium arsenide (AlGaAs), which may be used to produce infrared light. The specific wavelength within the 800 nanometer to 850 nanometer range may be achieved by varying the composition and structure of these semiconductor materials. The construction of the second light-emitting diodes 604A-N may involve the layering of these semiconductor materials to create a p-n junction, where electrons and holes recombine to emit light at the desired wavelength. The efficiency and color purity of the emitted light may be enhanced by optimizing the design and fabrication processes of the second light-emitting diodes 604A-N.

The plurality of first light-emitting diodes 602A-N and the plurality of second light-emitting diodes 604A-N may be arranged on the inner panel 800 in a checkerboard configuration. This arrangement may ensure that every other light-emitting diode on the inner panel 800 is a first light-emitting diode 602A-N, followed by a second light-emitting diode 604A-N, and so on. The checkerboard configuration may facilitate uniform light distribution across the target area by alternating the wavelengths emitted by the first light-emitting diodes 602A-N and the second light-emitting diodes 604A-N. The checkerboard pattern may also contribute to efficient heat dissipation and/or may prevent hotspots from forming on the inner panel 800. Each first light-emitting diode 602A-N and each second light-emitting diode 604A-N may be aligned with corresponding refraction means 606A-N to ensure optimal light direction and/or intensity.

The plurality of refraction means 606A-N may be optical components that direct and/or shape the emitted light from the plurality of first light-emitting diodes 602A-N and/or the plurality of second light-emitting diodes 604A-N away from the inner panel 800 of the narrow light distribution apparatus 600. The plurality of refraction means 606A-N may be made from transparent materials including but not limited to glass, silicon, and/or plastic. The plurality of refraction means 606A-N may comprise a substantially concave shape to produce light beams at beam angles between 25 degrees and 35 degrees. The plurality of refraction means 606A-N may be chosen for its optical clarity and/or resistance to heat and/or UV degradation which may ensure that the refraction means 606A-N maintain their shape and/or functional ability over time.

The refraction means 606A-N may be a substantially circular configuration. Additionally, the plurality of refraction means 606A-N may comprise components including but not limited to lenses, prisms, diffraction gratings, holographic optical elements, and/or fiber optic components. Each type of refraction means 606A-N may be selected based on the specific application requirements including but not limited to focusing, beam shaping, and/or spectral dispersion. The refraction means 606A-N may also be designed to optimize light transmission efficiency and/minimize optical aberrations.

Each of the plurality of refraction means 606A-N may be concave in shape and may produce a light beam comprising a beam angle between 25 degrees and/or 35 degrees when light from a corresponding light-emitting diode (e.g. one of the plurality of first light-emitting diodes 602A-N and/or one of the plurality of second light-emitting diodes 604A-N) passes through it. The concave shape of the refraction means 606A-N may bend the light rays inward, causing the light to converge and then diverge at a specific angle, according to one embodiment. As the corresponding light-emitting diode (e.g. one of the plurality of first light-emitting diodes 602A-N and/or one of the plurality of second light-emitting diodes 604A-N) emits light, the light beam may enter the concave surface of the refraction means 606A-N. The curvature of the concave surface may cause the light beam 1108 to refract and/or bend towards the central axis 1110 of the light beam 1108. This bending effect may focus the light beam 1108 into a narrower beam as it exits the refraction means 606A-N, according to one embodiment.

By carefully designing the curvature and material properties of the refraction means 606A-N, the emitted light may be shaped into the light beam 1108 with a desired angle, according to one embodiment. A more pronounced concave curvature may result in a tighter beam angle 1112, while a shallower curvature may produce a wider beam angle, according to one embodiment. The materials used for the refraction means 606A-N, which may include glass, silicon, and/or plastic, may also play a role in determining the refractive index, further influencing the beam angle 1112. The combination of these design elements ensures that the light passing through the refraction means 606A-N is directed and/or shaped to create a consistent beam angle 1112 between 25 degrees and 35 degrees, optimizing the light distribution for the intended application, according to one embodiment. The refraction means 606A-N may alter the direction and/or distribution of the light beam 1108 but may not change the wavelength of the light beam 1108, which is determined by the light-emitting diode 602, according to one embodiment.

The plurality of openings 608A-N may be apertures cut into the front panel 610 of the encasement 601. The plurality of openings 608A-N may each correspond to an individual light-emitting diode (e.g. one of the plurality of first light-emitting diodes 602A-N and/or one of the plurality of second light-emitting diodes 604A-N) and/or refraction means 606. The plurality of openings 608A-N may be aligned with the plurality of first light-emitting diodes 602A-N, the plurality of second light-emitting diodes 604A-N, and/or the plurality of refraction means 606A-N to allow the directed light from the plurality of first light-emitting diodes 602A-N and/or the plurality of refraction means 606A-N to be projected outwards to the area exterior to the narrow light distribution apparatus 600. The size, shape, and/or orientation of each of the plurality of openings 608A-N may be tailored to match the size, shape, and/or orientation of each of the refraction means 606A-N, the first light-emitting diodes 602A-N, and/or the second light-emitting diodes 604A-N. This precise alignment may ensure that the emitted light (e.g. the light beam 1108) is optimally directed and/or focused through the openings 608A-N.

The structural relationship between the openings 608A-N, the first light-emitting diodes 602A-N, the second light-emitting diodes 604A-N, and/or refraction means 606A-N may be critical for maintaining the efficiency and/or performance of the narrow light distribution apparatus 600, as misalignment may result in reduced light output and/or diminished therapeutic effects. The front panel 610 may incorporate reinforcement features adjacent to the plurality of openings 608A-N to maintain structural integrity and/or prevent deformation under operational stress. Additionally, the positioning and/or design of the openings 608A-N may facilitate efficient heat dissipation from the first light-emitting diodes 602A-N, which may contribute to the overall stability and longevity of the narrow light distribution apparatus 600.

The front panel 610 may be a structural component of the encasement 601 of the narrow light distribution apparatus 600. The front panel 610 may be a rectangular shape, a circular shape, an oval shape, a triangular shape, a rectangular shape, and/or any other shape. The front panel 610 may be made from materials including but not limited to metal, fiberglass, silicon, and/or plastic. The front panel 610 may comprise the plurality of openings 608A-N. The front panel 610 may house and/or align the first light-emitting diodes 602A-N and/or the refraction means 606A-N with the openings 608A-N. The front panel 610 may also include mounts and/or supports for securing the plurality of first light-emitting diodes 602A-N and/or refraction means 606A-N in place. These mounts and/or supports may be designed to provide precise positioning and/or stability which may ensure that the first light-emitting diodes 602A-N and/or refraction means 606A-N remain properly aligned during operation.

The front panel 610 may be formed from a single mold process. The front panel 610 may be attached to the siding 614 of the encasement 601 using fastening methods including but not limited to screws, bolts, adhesive bonding, and/or snap-fit mechanisms. This attachment may ensure a secure connection that may maintain the integrity of the encasement 601 and/or provide a stable environment for the internal components. Additionally, the front panel 610 may feature integrated channels and/or pathways to accommodate wiring and/or other connections necessary for the operation of the first light-emitting diodes 602A-N and/or refraction means 606A-N. The front panel 610 and/or back panel 200 may attach to the siding 614 to create a secure enclosure and/or interencasement space.

The control panel 612 may be an interface equipped with controls for adjusting the settings of the narrow light distribution apparatus 600, including but not limited to power on/off, light intensity levels, and/or timing functions. The control panel 612 may comprise buttons, switches, and/or touch-sensitive elements. This control panel 612 may include a microcontroller and/or other electronic circuitry to manage the various functions and/or settings of the narrow light distribution apparatus 600. The control panel 612 may be located on the siding 614 of the encasement 601. The control panel 612 may be designed to provide feedback to the user through indicators including but not limited to LED lights, displays, and/or audible signals. The integration of the control panel 612 with the siding 614 may ensure that the internal components are neatly organized and that the wiring and connections to the microcontroller and other electronic circuitry are secure and well-protected. This integration may also help maintain the overall structural integrity and/or aesthetic appearance of the narrow light distribution apparatus 600.

The siding 614 may be the area between the front panel 610 and/or the back panel 200. The siding 614 may form the lateral boundaries of the encasement 601. The siding 614 may be positioned at the outermost edges of the front panel 610 and/or the back panel 200. The siding 614 may comprise the right side 616, the left side 618, the bottom 620, and/or the top 622. The siding 614 may create a contiguous structure around the inner panel 800 (not shown) and/or other internal components. The siding 614 may be formed from a single mold process. Alternatively, the siding 614 may comprise a plurality of separate components attached to one another which may provide flexibility in manufacturing and/or assembly. The siding 614 may have a width that is wider than the inner panel 800 to ensure the inner panel 800 fits properly within the interencasement space 1000.

The siding 614 may be comprised of the same material as the front panel 610 and/or the back panel 200. The siding 614 may be securely joined to the front panel 610 and/or the back panel 200 using screws, bolts, adhesive bonding, and/or snap-fit mechanisms. The siding 614, the front panel 610, and/or the back panel 600 may be jointly formed in a single mold process or in a modular assembly process to accommodate different design and/or manufacturing requirements. Additionally, the siding 614 may comprise the side vent 624 which may facilitate airflow and/or cooling within the encasement 601.

The right side 616 may be one of the vertical sides of the siding 614 of the encasement 601. The right side 616 may be made from the same material as the front panel 610, the back panel 200, and/or the rest of the siding 614, which may ensure consistency in material properties and aesthetic appearance. The right side 616 may also include mounting points and/or brackets for securing the narrow light distribution apparatus 600 in place during use, which may provide stability and ease of installation.

The left side 618 may be one of the vertical sides of the siding 614 of the encasement 601. The left side 618 may be made from the same material as the front panel 610, the back panel 200, and/or the rest of the siding 614, which may maintain uniformity in design. The left side 618 may also include mounting points and/or brackets for securing the narrow light distribution apparatus 600 in place during use, which may ensure reliable positioning and support.

The bottom 620 may be the lowermost horizontal portion of the siding 614 of the encasement 601. The bottom 620 may be made from the same material as the front panel 610, the back panel 200, and/or the rest of the siding 614, which may contribute to the overall structural coherence. The bottom 620 may also include mounting points and/or brackets for securing the narrow light distribution apparatus 600 in place during use, which may provide a stable foundation.

The top 622 may be the uppermost horizontal portion of the siding 614 of the encasement 601. The top 622 may be made from the same material as the front panel 610, the back panel 200, and/or the rest of the siding 614, which may ensure a cohesive and robust construction. The top 622 may also include mounting points and/or brackets for securing the narrow light distribution apparatus 600 in place during use, which may facilitate secure attachment and stability.

The side vent 624 may be an opening/openings located on the siding 614 of the encasement 601. The side vent 624 may facilitate airflow into and/or out of the interencasement space 1000, which may aid in the cooling of internal components including but not limited to the first light-emitting diodes 602A-N, the inner panel 800, and/or other electronic parts and components. This ventilation may be critical for maintaining optimal operating temperatures and ensuring the longevity and performance of the narrow light distribution apparatus 600.

According to one embodiment, FIG. 6 shows a narrow light distribution apparatus 600 comprising an encasement 601. The encasement may comprise a front panel 610, a back panel 700 (not shown), and/or a siding 614. The encasement 601 may be a substantially cuboid shape.

The narrow light distribution apparatus 600 may comprise a plurality of refraction means 606A-N. Each refraction means 606A-N may be aligned with one or more of the plurality of first light-emitting diodes 602A-N and/or one or more of the plurality of second light-emitting diodes 604A-N to direct light emitted from the first light-emitting diodes 602A-N and/or the plurality of second light-emitting diodes 604A-N away from the inner panel 800. Each of the plurality of refraction means 606A-N may be concave in shape and may produce a light beam 1108 comprising a beam angle 1614 between 25 degrees and/or 35 degrees when light from the corresponding first light-emitting diode 602 passes through it. Each of the plurality of first light-emitting diodes 602A-N may emit light comprising a wavelength between 600 nanometers and 650 nanometers. Each of the plurality of first light-emitting diodes 602A-N may have a wattage between four watts and/or six watts.

The narrow light distribution apparatus 600 may comprise a plurality of openings 608A-N that may be cut into the front panel 610. Each opening 608 may be aligned with one of the plurality of first light-emitting diodes 602A-N, one of the plurality of second light-emitting diodes 604A-N, one of the plurality of refraction means 606A-N, and/or one of the plurality of housings 804A-N. The narrow light distribution apparatus 600 may comprise a control panel 612 to control at least one of an on/off switch, light intensity, and/or a timer.

Figure 7:
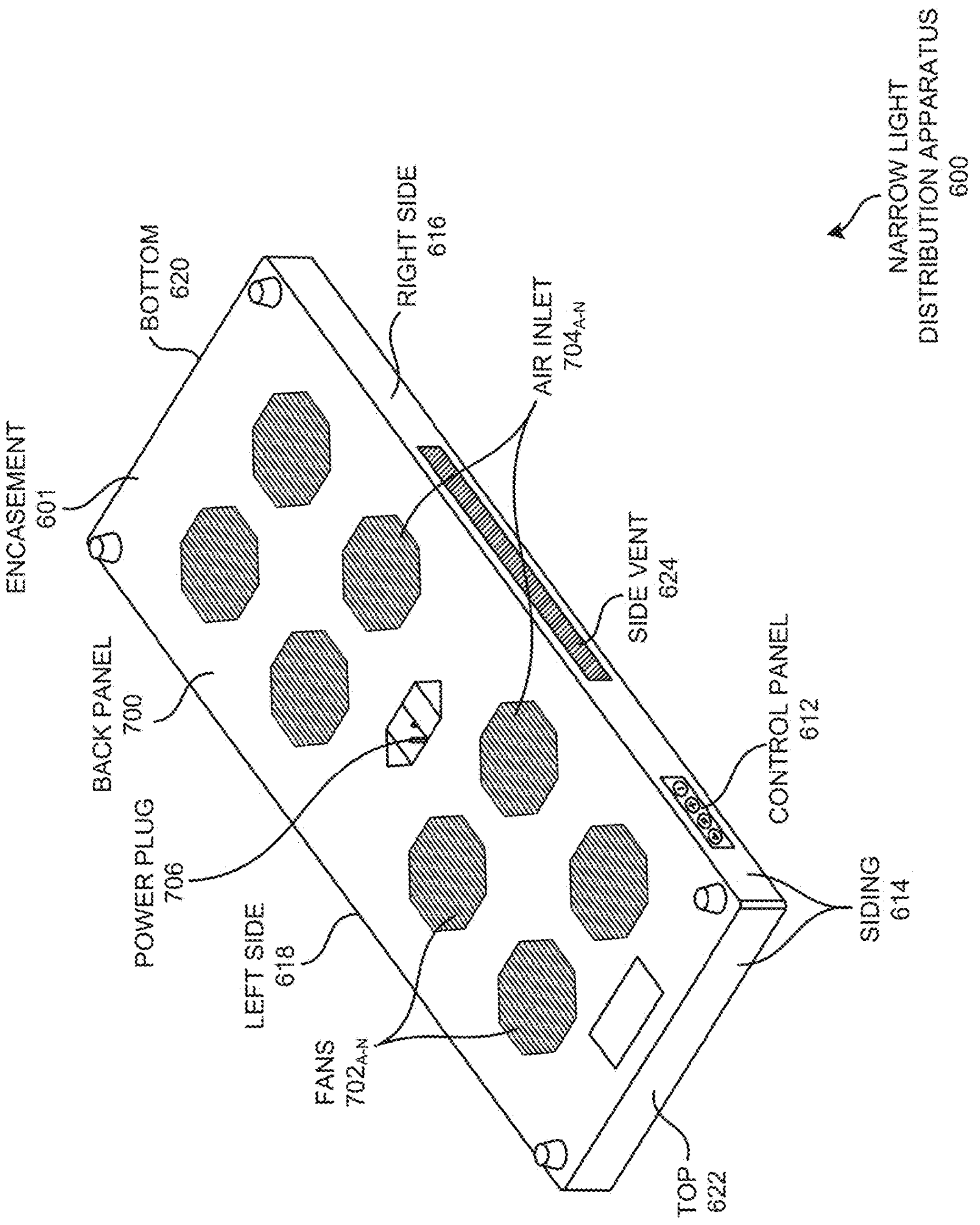
FIG. 7 is a rear top right side perspective view of the narrow light distribution apparatus of FIG. 6, according to one embodiment.

FIG. 7 is a rear top right side perspective view of the narrow light distribution apparatus 600 of FIG. 6, according to one embodiment. FIG. 7 illustrates the narrow light distribution apparatus 600, the encasement 601, control panel 612, the siding 614, the right side 616, the left side 618, the bottom 620, the top 622, the side vent 624, a back panel 700, a plurality of fans 702A-N, a plurality of air inlets 704A-N, and a power plug 706.

The back panel 700 may be a structural component of the encasement 601. The back panel 700 may be made from materials including but not limited to metal, fiberglass, silicon, and/or plastic. The back panel 700 may comprise a plurality of air inlets 704A-N, which may be openings and/or vents cut into the back panel 700 to allow air to enter and/or flow through the narrow light distribution apparatus 600, aiding in cooling the various components. The back panel 700 may also include a power plug 706, electrical connectors, mounting brackets, and/or additional support structures.

The back panel 700 may connect to the siding 612 of the encasement 601 using fasteners, adhesives, and/or interlocking mechanisms. The connection points may be designed to provide a secure and stable attachment, ensuring the structural integrity of the encasement 601. The back panel 700 may be attached to the siding 612 by aligning the edges of the back panel 700 with the corresponding edges of the siding 612 and securing them with screws, bolts, and/or adhesive bonding. This connection method may ensure that the back panel 700 is firmly held in place, providing support for the internal components and maintaining the overall shape and functionality of the narrow light distribution apparatus 600.

In some embodiments, the back panel 700, the siding 612, and the front panel 608 of the encasement 601 may be formed in a single mold process. This integrated molding process may use materials such as plastic or fiberglass to create a single, seamless unit, enhancing the structural integrity and reducing the need for additional fasteners or adhesives. The single mold process may ensure precise alignment and fitting of all components, resulting in a robust and aesthetically pleasing encasement 601.

The plurality of fans 702A-N may be cooling devices installed within the interencasement space 1000 of the encasement 601 to dissipate heat generated by the first light-emitting diodes 602A-N, the plurality of second light-emitting diodes 604A-N, and/or other electronic components. The fans 702A-N may vary in type, including but not limited to axial fans, which may be designed to move air parallel to the axis of the fan, and/or centrifugal fans, which move air perpendicular to the intake of the fan. These fans 702A-N may be made from materials including but not limited to plastic and/or metal, with blades designed for optimal airflow and minimal noise. The fans 702A-N may be strategically placed to ensure efficient cooling to prevent overheating and/or to maintain the performance and longevity of the narrow light distributor 600.

The plurality of air inlets 704A-N may be openings and/or vents cut into the back panel 200 of the encasement 601 to allow air to enter and/or flow through the narrow light distributor 600 which may aid in cooling the various components of the narrow light distribution apparatus 600. The air inlets 704A-N may be designed with filters to prevent dust and/or debris from entering the interencasement space 1000 of the encasement 601 which may ensure clean airflow. The air inlets 704A-N may vary in shape and/or size depending on the cooling requirements of the apparatus, and they may be positioned adjacent to the fans 702A-N to maximize airflow and/or cooling efficiency.

The power plug 706 may be an electrical connector that provides the narrow light distributor 600 with a connection to an external power source. The power plug 706 may be designed to accommodate various types of electrical outlets, including but not limited to standard AC plugs for residential and/or commercial use, or specialized plugs for industrial applications. The power plug 706 may be made from durable materials including but not limited to thermoplastic and/or rubber which may ensure safety and/or longevity. Additionally, the power plug 706 may include features including but not limited to a fuse and/or surge protector to safeguard the narrow light distributor 600 against electrical faults and/or surges.

According to one embodiment, FIG. 7 shows the narrow light distribution apparatus 600 comprising a plurality of fans 702A-N that may be positioned within the interencasement space 1000 (not shown) between a backside 1002 (not shown) of the inner panel 800 and/or the back panel 700 to cool the narrow light distribution apparatus 600. A plurality of air inlets 704A-N may be cut into the back panel 700. Each air inlet 704 may be positioned substantially adjacent to at least one of the plurality of fans 702A-N. The siding 614 (e.g. the right side 616, the left side 618, the bottom 620 and/or the top 622) may be attached to the back panel 700 of the encasement 601 at the outermost portion of the back panel 700.

The power plug 706 may be integrated into the back panel 700 and may allow the narrow light distribution apparatus 600 to be electronically connected to a power source. Electrical power may move from the power source, through power plug 706, and to the various electrical components of the narrow light distribution apparatus 600 (e.g. the electrical sockets 802A-N, the housings 804A-N, the first light-emitting diodes 602A-N, the plurality of second light-emitting diodes 604A-N, the control panel 612, the fans 702A-N, etc.).

Figure 8:
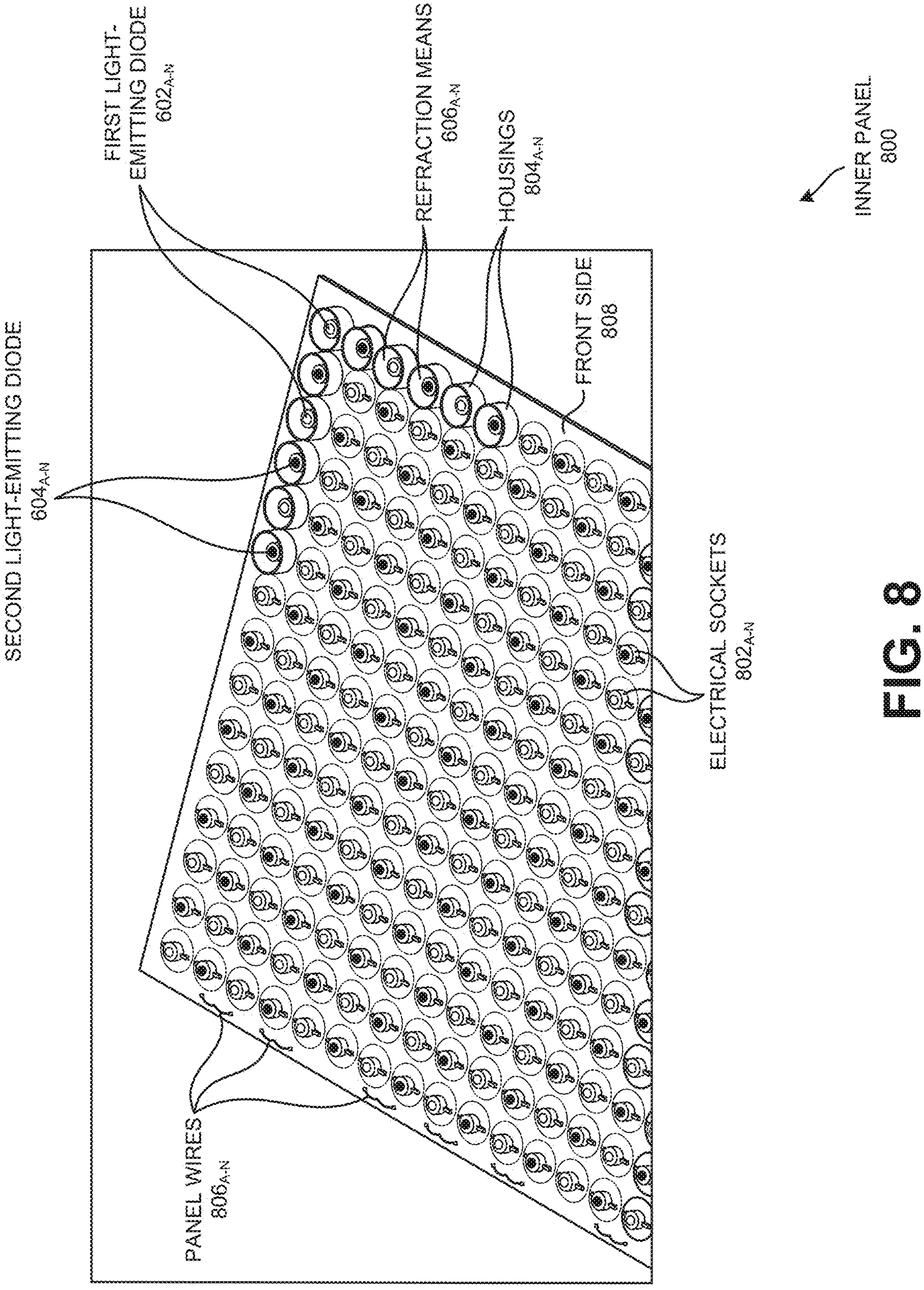
FIG. 8 is a front bottom right side perspective view of the inner panel of the narrow light distribution apparatus of FIGS. 6-7, according to one embodiment.

FIG. 8 is a front bottom right side perspective view of the inner panel 800 of the narrow light distribution apparatus 600 of FIGS. 6-7, according to one embodiment. FIG. 8 illustrates the narrow light distribution apparatus 600 comprising the plurality of first light-emitting diodes 602A-N, the plurality of second light-emitting diodes 604A-N, the plurality of refraction means 606A-N, an inner panel 800, a plurality of electrical sockets 802A-N, a plurality of housings 804A-N, one or more panel wire 806A-N, and a front side 808.

The inner panel 800 may be a structural and/or electrical component situated within the interencasement space 1000 of the narrow light distribution apparatus 600. The inner panel 800 may comprise the electrical sockets 802A-N, the one or more panel wire 806A-N, the front side 808, and/or a backside 1002 (not shown). The inner panel 800 may be made from materials including but not limited to metals (including but not limited to zinc, aluminum, steel, and/or copper), silicon, ceramics, and/or high-strength plastic to provide a sturdy mounting surface for the electrical components and/or a surface with cooling properties.

The inner panel 800 may serve as a central platform to which various electrical and/or optical components are attached including but not limited to the first light-emitting diodes 602A-N, the plurality of second light-emitting diodes 604A-N, the housings 804A-N and/or the one or more panel wire 806A-N. The inner panel 800 may be a shape substantially corresponding to the shape of the encasement 601 including but not limited to a rectangle, oval, circle, and/or any other shape. The inner panel 800 may also include integrated pathways and/or channels for the one or more panel wire 806A-N which may allow the one or more panel wire 806A-N to run power to each of the electrical sockets 802A-N.

The plurality of electrical sockets 802A-N may be electrical and/or mechanical connection points for the housings 804A-N. The plurality of electrical sockets 802A-N may be located on the front side 808 of the inner panel 800. The electrical sockets 802A-N may be designed to receive and/or secure the housings 804A-N for the first light-emitting diodes 602A-N and/or the second light-emitting diodes 604A-N. The plurality of electrical sockets 802A-N may provide electrical connections to power the first light-emitting diodes 602A-N and/or the plurality of second light-emitting diodes 604A-N from the power source. The electrical sockets 802A-N may vary in type, including standard sockets, which may provide simple plug-and-play connections, and/or locking sockets, which may offer more secure and/or stable connections to prevent accidental disconnections during operation. The plurality of electrical sockets 802A-N may be made from conductive materials including but not limited to copper and/or brass which may ensure efficient electrical conductivity.

The electrical sockets 802A-N may conform to industry standards, utilizing connectors such as normal American kettle lead plugs, IEC connectors, NEMA connectors, and/or custom-designed connectors, with proper earthing in the center of the inner panel 800. The electrical sockets 802A-N may be housed in insulating materials such as plastic, which may ensure safe and/or reliable electrical connections by preventing electrical shorts and/or protecting the internal components from potential damage. Additionally, the plurality of electrical sockets 802A-N may include features such as polarization to ensure correct orientation during connection, and/or integrated strain relief to prevent damage to the wires and connectors. The electrical sockets 802A-N may be arranged in a specific pattern on the front side 808 of the inner panel 800, such as a grid or staggered configuration, to optimize the layout and ensure uniform light distribution from the first light-emitting diodes 602A-N and/or the plurality of second light-emitting diodes 604A-N. The design and placement of the electrical sockets 802A-N may facilitate easy maintenance and replacement of individual first light-emitting diodes 602A-N, individual second light-emitting diodes 604A-N, and/or the housings 804A-N.

The plurality of electrical sockets 802A-N may be arranged in various configurations on the inner panel 800, including but not limited to a grid pattern. The electrical sockets 802A-N, along with the housings 804A-N, the first light-emitting diodes 602A-N, the second light-emitting diodes 604A-N, and refraction means 606A-N, may be configured in patterns such as concentric circles, staggered rows, and/or custom designs tailored to specific light distribution needs. The housings 804A-N may be made from materials including but not limited to metal, plastic, and/or ceramic, which may provide protection against environmental factors and/or help dissipate heat generated by the first light-emitting diodes 602A-N and/or the second light-emitting diodes 604A-N.

The plurality of housings 804A-N may be protective, supportive, and/or conductive structures that electrically connect, mechanically connect, and/or protect the plurality of first light-emitting diodes 602A-N and/or the plurality of second light-emitting diodes 604A-N. The plurality of housings 804A-N may each be designed to hold an individual first light-emitting diode 602A-N and/or an individual second light-emitting diode 604A-N. The housings 804A-N may comprise prongs and/or mounts that fit into the electrical sockets 802A-N. These prongs of the housings 804A-N may ensure that the housings 804A-N, the first light-emitting diodes 602A-N, and/or the second light-emitting diodes 604A-N are mounted to the inner panel 800 and/or properly aligned with the refraction means 606A-N and/or openings 608A-N in the front panel 610. The housings 804A-N may be cylindrical, cuboid, or other shapes tailored to specific design requirements which may provide versatility in their application.

Additionally, the housings 804A-N may facilitate the transfer of electrical power from the electrical sockets 802A-N to the first light-emitting diodes 602A-N and/or the second light-emitting diodes 604A-N. This power transfer may occur through conductive pathways integrated within the housings 804A-N, which may ensure efficient delivery of electricity to the first light-emitting diodes 602A-N and/or the second light-emitting diodes 604A-N. The design of the housings 804A-N may also incorporate features to optimize the alignment and stability of the first light-emitting diodes 602A-N and/or the second light-emitting diodes 604A-N, enhancing the overall performance and reliability of the narrow light distribution apparatus 600.

The one or more panel wire 806A-N may be an electrical conductor that connects various components within the narrow light distribution apparatus 600. The one or more panel wire 806A-N may be made from materials including but not limited to copper and/or aluminum. The one or more panel wire 806A-N may be insulated with materials including but not limited to PVC and/or silicone to prevent short circuits and/or protect against electrical shocks. The one or more panel wire 806A-N may run from the power source to the electrical sockets 802A-N. The one or more panel wire 806A-N may also be routed through designated pathways in the inner panel 800 to keep the internal layout organized and/or minimize the risk of damage.

The one or more panel wire 806A-N may be attached to the inner panel 800 using various fastening methods including but not limited to clips, clamps, and/or adhesive channels. These attachment methods may secure the one or more panel wire 806A-N in place, preventing movement and reducing the risk of wear and tear due to vibrations or handling, according to one embodiment. The designated pathways in the inner panel 800 may be pre-formed channels or grooves specifically designed to accommodate the one or more panel wire 806A-N, ensuring a neat and orderly arrangement, according to one embodiment.

Additionally, the one or more panel wire 806A-N may be integrated with the inner panel 800 through embedded conduits or molded pathways. These integrated features may provide a streamlined and/or protected route for the one or more panel wire 806A-N, enhancing the durability and reliability of the electrical connections, according to one embodiment. The integration of the one or more panel wire 806A-N with the inner panel 800 may facilitate efficient assembly and/or maintenance of the narrow light distribution apparatus 600 by ensuring that the wiring is systematically organized and/or securely held in place.

The one or more panel wire 806A-N may terminate at the electrical sockets 802A-N, where they may be connected to provide power to the plurality of first light-emitting diodes 602A-N and/or the plurality of second light-emitting diodes 604A-N. These connections may be made using soldering, crimping, and/or plug-and-socket connectors, ensuring reliable electrical contact and easy assembly or replacement. The overall design of the one or more panel wire 806A-N integration with the inner panel 800 may prioritize safety, case of assembly, and/or long-term reliability.

The front side 808 may be the surface of the inner panel 800 that faces the front panel 610 of the encasement 601. The front side 808 may comprise the electrical sockets 802A-N, which may be integrated directly onto this surface. The front side 808 may ensure that the electrical sockets 802A-N, and thus the housings 804A-N, the first light-emitting diodes 602A-N, the second light-emitting diodes 604A-N, and/or the refraction means 606A-N, are properly aligned with the openings 608A-N of the front panel 610. The front side 808 may include markings and/or guides to facilitate the precise installation and alignment of the sockets 802A-N and/or housings 804A-N. These markings and/or guides may ensure that the electrical sockets 802A-N, housings 804A-N, first light-emitting diodes 602A-N, the second light-emitting diodes 604A-N, and/or refraction means 606A-N are correctly positioned for optimal light emission and/or performance. The front side 808 may be treated and/or coated to enhance its durability and/or resistance to environmental factors, which may ensure long-term reliability and performance of the narrow light distribution apparatus 600.

According to one embodiment, FIG. 8 shows the narrow light distribution apparatus 600 comprising an inner panel 800 situated within the interencasement space 1000 (not shown). The inner panel 800 of the narrow light distribution apparatus 600 may comprise a plurality of electrical sockets 802A-N that may be arranged on a front side 808 of the inner panel 800. The electrical sockets 802A-N of the inner panel 800 may be electrically connected to a power source.

The inner panel 800 of the narrow light distribution apparatus 600 may further comprise a plurality of housings 804A-N. Each housing 804 may be individually attached to one of the plurality of first electrical sockets 802A-N. The narrow light distribution apparatus 600 may further comprise a plurality of first light-emitting diodes 602A-N and/or a plurality of second light-emitting diodes 604A-N. Each first light-emitting diode 602 may be at least partially within one individual housing 804. Each second light-emitting diode 604 may be at least partially within one individual housing 804 One first light-emitting diode 602 may be transposed at least partially within one individual housing 804, according to one embodiment. One second light-emitting diode 604 may be transposed at least partially within one individual housing 804, according to one embodiment. The plurality of housings 804A-N may protect the plurality of first light-emitting diodes 602A-N and/or the plurality of second light-emitting diodes 604A-N. The plurality of housings 804A-N may move power from the electrical sockets 802A-N to the first light-emitting diodes 602A-N and/or the second light-emitting diodes 604A-N.

The inner panel 800 of the narrow light distribution apparatus 600 may comprise one or more panel wire 806A-N to electrically connect the power source to the plurality of first light-emitting diodes 602A-N and/or the plurality of second light-emitting diodes 604A-N via the plurality of electrical sockets 802A-N and/or the plurality of housings 804A-N. When the power source is delivering power to the plurality of electrical sockets 802A-N, the first light-emitting diodes 602A-N and/or the plurality of second light-emitting diodes 604A-N may be powered and/or emit light through the refraction means 606A-N and/or the openings 608A-N to an area exterior to the narrow light distribution apparatus 600.

The plurality of electrical sockets 802A-N, the plurality of first light-emitting diodes 602A-N, the plurality of second light-emitting diodes 604A-N, the plurality of refraction means 606A-N, and/or the plurality of openings 608A-N may be arranged in a checkered configuration. Furthermore, the plurality of electrical sockets 802A-N, the plurality of first light-emitting diodes 602A-N, the plurality of second light-emitting diodes 604A-N, the plurality of refraction means 606A-N, and/or the plurality of openings 608A-N may be arranged in a fifteen unit by forty unit configuration. For example, according to one embodiment, the narrow-light distribution apparatus 600 may be configured as follows: fifteen corresponding sockets 802A-N, fifteen housings 804A-N, fifteen light-emitting diodes (e.g. the plurality of first light-emitting diodes 602A-N and/or the plurality of second light-emitting diodes 604A-N), and fifteen refractions means 606A-N wide by forty corresponding sockets 802A-N, forty housings 804A-N, forty light-emitting diodes (e.g. the plurality of first light-emitting diodes 602A-N and/or the plurality of second light-emitting diodes 604A-N), and/or forty refractions means 606A-N tall, according to one embodiment.

Figure 9:
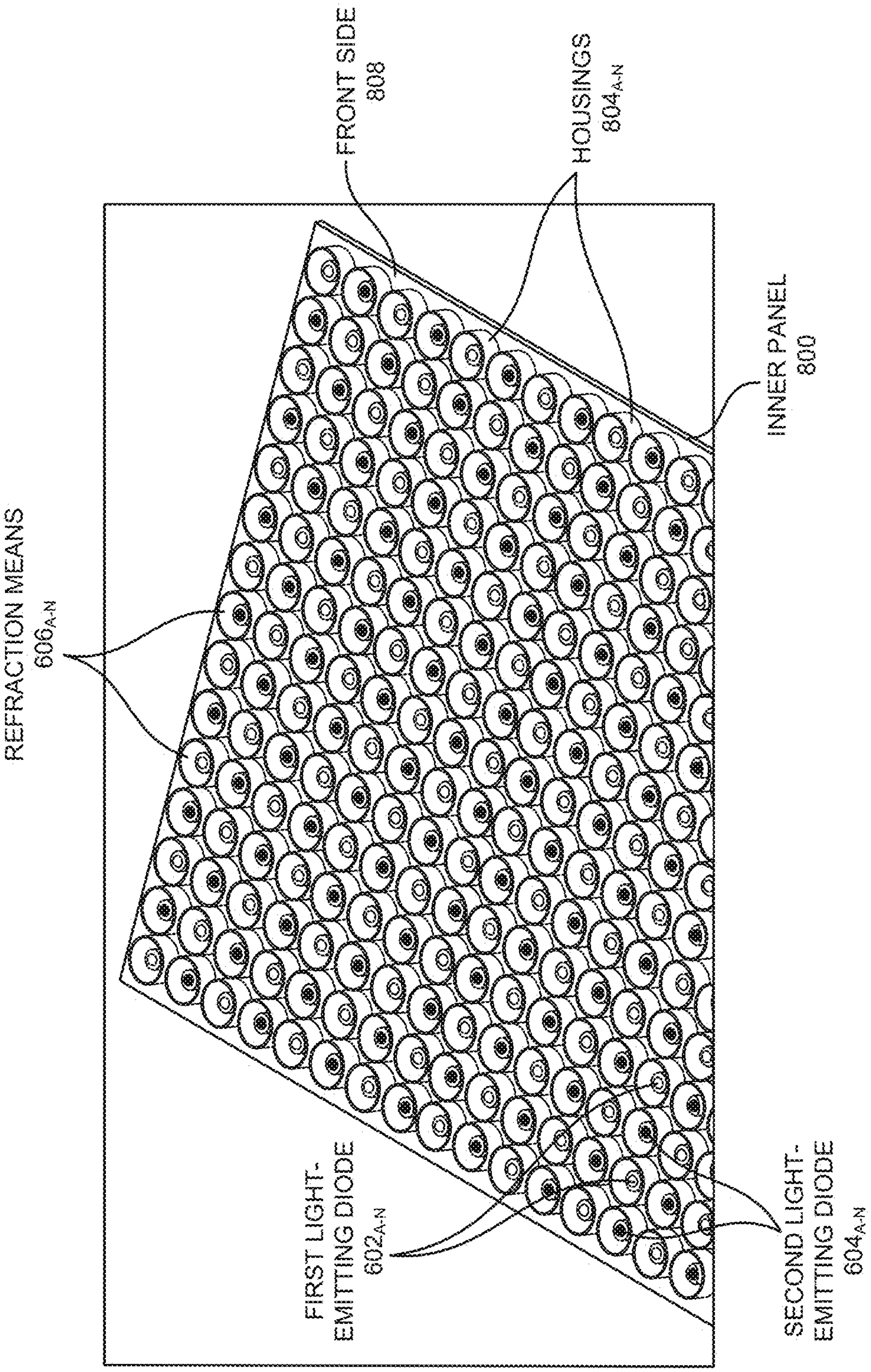
FIG. 9 is a partial view of the inner panel of the narrow light distribution apparatus of FIGS. 6-8, according to one embodiment.

FIG. 9 is a partial view of the inner panel 800 of the narrow light distribution apparatus 600 of FIGS. 6-8, according to one embodiment. FIG. 9 illustrates the plurality of first light-emitting diodes 602A-N, the plurality of second light-emitting diodes 604A-N, the plurality of refraction means 606A-N, the inner panel 800, the plurality of housings 804A-N, and the front side 808.

According to one embodiment, FIG. 9 shows a partial view of the inner panel 800 of the narrow light distribution apparatus 600. The inner panel 800 may comprise a plurality of first light-emitting diodes 602A-N, a plurality of second light-emitting diodes 604A-N, a plurality of refraction means 606A-N, a plurality of housings 804A-N, and a front side 808. The first light-emitting diodes 602A-N may emit light in specific wavelengths ranging from 600 nanometers to 650 nanometers, while the second light-emitting diodes 604A-N may emit light in specific wavelengths ranging from 800 nanometers to 850 nanometers. The refraction means 606A-N may be optical components that direct and/or shape the emitted light (e.g. the light beam 1108 from both the first and/or second light-emitting diodes 602A-N and 604A-N. The housings 804A-N may be protective, supportive, and/or conductive structures that electrically connect, mechanically connect, and/or protect the first and/or second light-emitting diodes 602A-N and 604A-N. The front side 808 may be the surface of the inner panel 800 that faces the front panel 610 of the encasement 601. The alignment and/or arrangement of these components on the inner panel 800, in a checkerboard configuration, may ensure optimal light emission and/or performance of the narrow light distribution apparatus 600, according to one embodiment.

Figure 10:
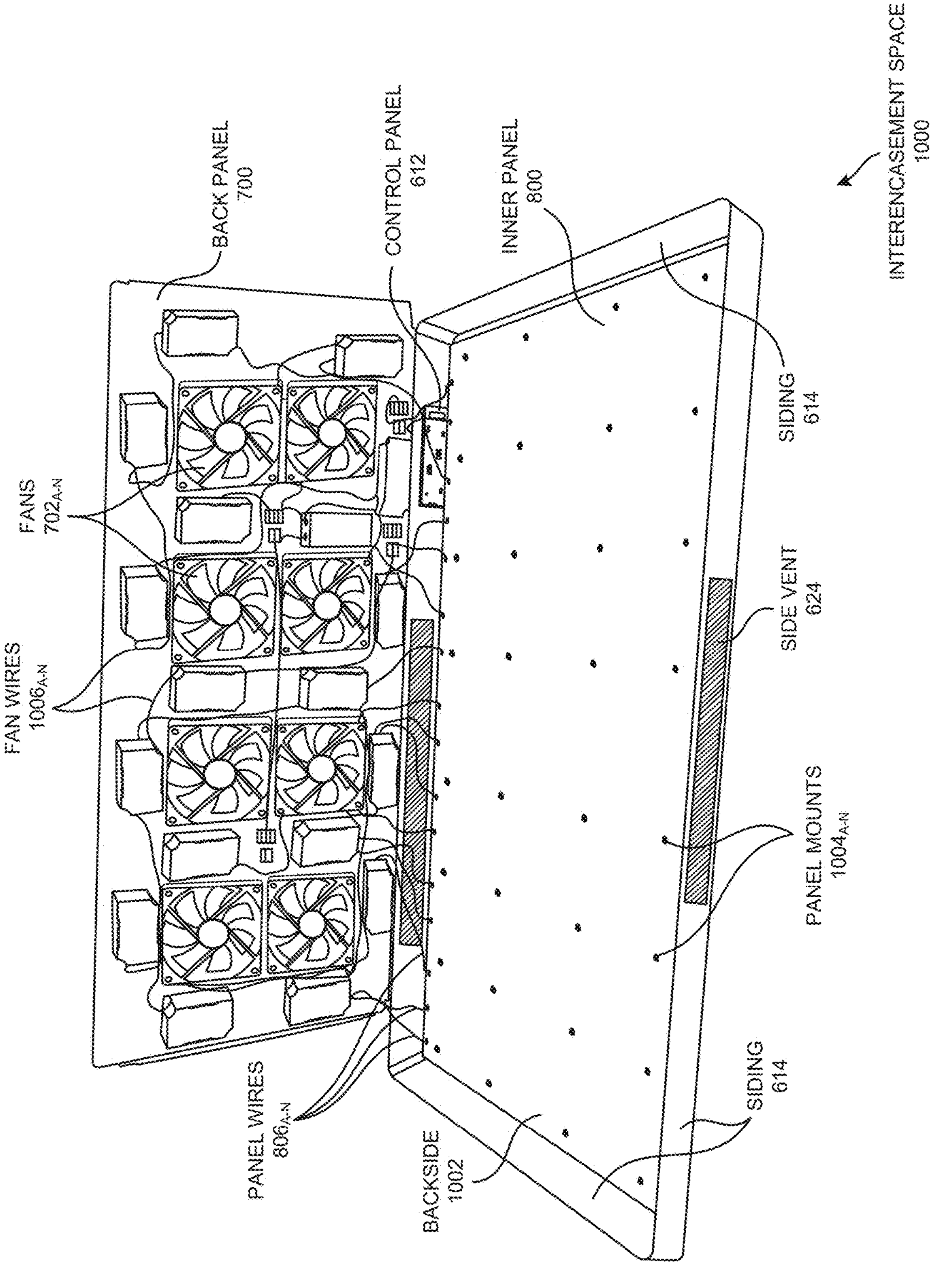
FIG. 10 is a detailed view of the inner components and structure of the narrow light distribution apparatus of FIGS. 6-9, according to one embodiment.

FIG. 10 is a detailed view of the inner components and structure of the narrow light distribution apparatus 600 of FIGS. 6-9, according to one embodiment. FIG. 10 illustrates the narrow light distribution apparatus 600 comprising the control panel 612, the siding 614, the side vent 624, the back panel 700, the fans 702A-N, the inner panel 800, the panel wires 806A-N, an interencasement space 1000, a backside 1002, a plurality of panel mounts 1004A-N, and a plurality of fan wires 1006A-N.

The interencasement space 1000 may be the internal area formed when the front panel 610 and the back panel 200 are attached to the siding 614. The interencasement space 1000 may house various internal components, including but not limited to the inner panel 800, the electrical sockets 802A-N, the housings 804A-N, the one or more panel wire 806A-N, the refraction means 606A-N, the first light-emitting diodes 602A-N, the second light-emitting diodes 604A-N, the fans 702A-N, the fan wires 1006A-N, the panel mounts 1004A-N and/or other components. The interencasement space 1000 may provide an organized layout for the various components of the narrow light distribution apparatus 600, which may ensure that each element is securely mounted and/or properly aligned. The interencasement space 1000 may also facilitate efficient airflow, aided by the plurality of fans 702A-N, which may prevent overheating and/or maintain optimal performance of the first light-emitting diodes 602A-N, the second light-emitting diodes 604A-N, and/or other electronic parts. Additionally, the interencasement space 1000 may include pathways for wiring and/or may accommodate various control mechanisms to regulate the operation of the device.

The backside 1002 may be the rear surface of the inner panel 800. The backside 1002 may support the integration of various components, including but not limited to the electrical sockets 802A-N and/or housings 804A-N. The backside 1002 may also include pathways for wiring and/or other connections, which may ensure that electrical and/or mechanical connections remain organized and/or accessible.

The plurality of panel mounts 1004A-N may be structural elements used to secure different components within the interencasement space 1000. The plurality of panel mounts 1004A-N may attach to the inner panel 800 and/or the back panel 200. The plurality of panel mounts 1004A-N may connect other structural parts, which may ensure stability and/or proper alignment of the internal components. The placement and design of the panel mounts 1004A-N may facilitate the secure attachment of various elements within the interencasement space 1000.

The plurality of fan wires 1006A-N may be electrical conductors that connect the fans 702A-N to the power source and/or control panel 612. The plurality of fan wires 1006A-N may run through designated pathways in the inner panel 800 and/or other structural elements. The plurality of fan wires 1006A-N may provide power and/or control signals to the fans 702A-N, which may ensure efficient cooling of the first light-emitting diodes 602A-N, the second light-emitting diodes 604A-N, and/or other heat-generating components. The routing of the fan wires 1006A-N may optimize airflow and/or minimize interference with other components.

According to one embodiment, FIG. 10 shows the narrow light distribution apparatus 600 comprising an interencasement space 1000 within the encasement 601 that may be formed when the front panel 610 and/or the back panel 700 are attached to the siding 614. The plurality of fans 702A-N may be positioned within the interencasement space 1000 between a backside 1002 of the inner panel 800 and/or the back panel 700 to cool the narrow light distribution apparatus 600. The plurality of fans 702A-N may be electrically connected to the power source via a plurality of fan wires 1006A-N. The plurality of fans 702A-N may also be communicatively coupled to the control panel 612 (not shown) via the plurality of fan wires 1006A-N.

Figure 11:
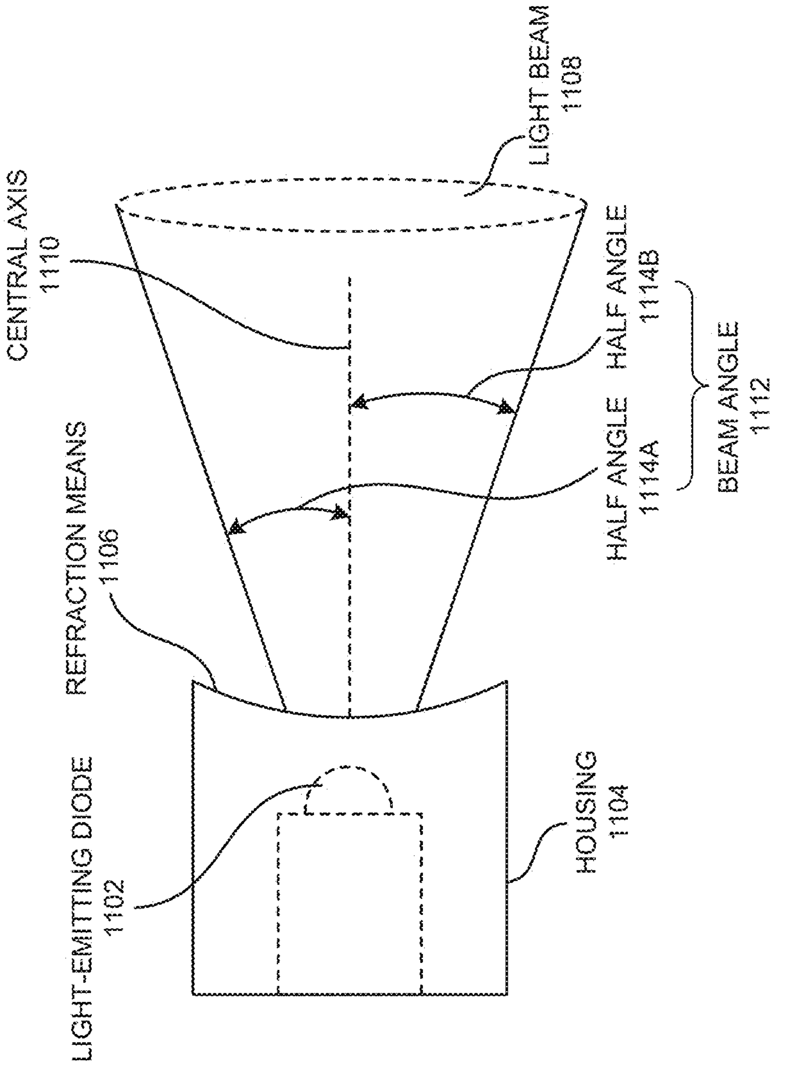
FIG. 11 is a profile view of one of the light-emitting diodes of the narrow light distribution apparatus of FIGS. 1-5 and FIGS. 6-10, according to one embodiment.

FIG. 11 is a profile view of one of the light-emitting diodes (e.g. the light-emitting diodes 102A-N, the first light-emitting diodes 602A-N, and/or the second light-emitting diodes 604A-N) of the narrow light distribution apparatus of FIGS. 1-5 and FIGS. 6-10, according to one embodiment. FIG. 11 illustrates a light-emitting diode 1102, a housing 1104, a refraction means 1106, a light beam 1108, a central axis 1110, and a beam angle 1112 comprising a half angle 1114A and a half angle 1114B.

The light-emitting diode 1102 may be at least one of the light-emitting diodes 102A-N, the first light-emitting diodes 602A-N, and/or the second light-emitting diodes 604A-N. The housing 1104 may be at least one of the housings 304A-N and/or the housings 804A-N. The refraction means 1106 may be at least one of the refraction means 104A-N and/or the refraction means 606A-N.

The light beam 1108 may be light from the light-emitting diode 1102 that has been shaped and/or directed by the refraction means 1106, according to one embodiment. The beam angle 1112 may be the full angular width of the light beam where the light intensity falls to 50% of the maximum, also known as the Full Width at Half Maximum (FWHM). The beam angle 1112 may be between 25 degrees and 35 degrees, ensuring effective light dispersion.

The central axis 1110 may be the centerline running through the middle of the light beam 1108 from the light-emitting diode 1102. The half angle 1114A may represent half of the total beam angle 1112 on one side of the central axis 1110, and the half angle 1114B may represent the other half on the opposite side, together forming the complete beam angle 1112. For example, if the beam angle 1112 is 30 degrees, then each half angle 1114A and 1114B would be 15 degrees. To achieve a beam angle between 25 degrees and 35 degrees, each half angle 1114A and 1114B must be between 12.5 degrees and 17.5 degrees.

The refraction means 1106 may work to achieve this beam angle by bending the light rays emitted from the light-emitting diode 1102 inwards towards the central axis 1110. This bending effect, also known as refraction, may focus the light rays into a narrower beam. The refraction means 1106 may be designed with specific curvature and/or material properties to control the degree of bending and ensure that the light is directed within the desired beam angle range. This precise control over the light direction and dispersion helps in achieving uniform illumination and optimal performance for various applications of the narrow light distribution apparatus.

Figure 12:
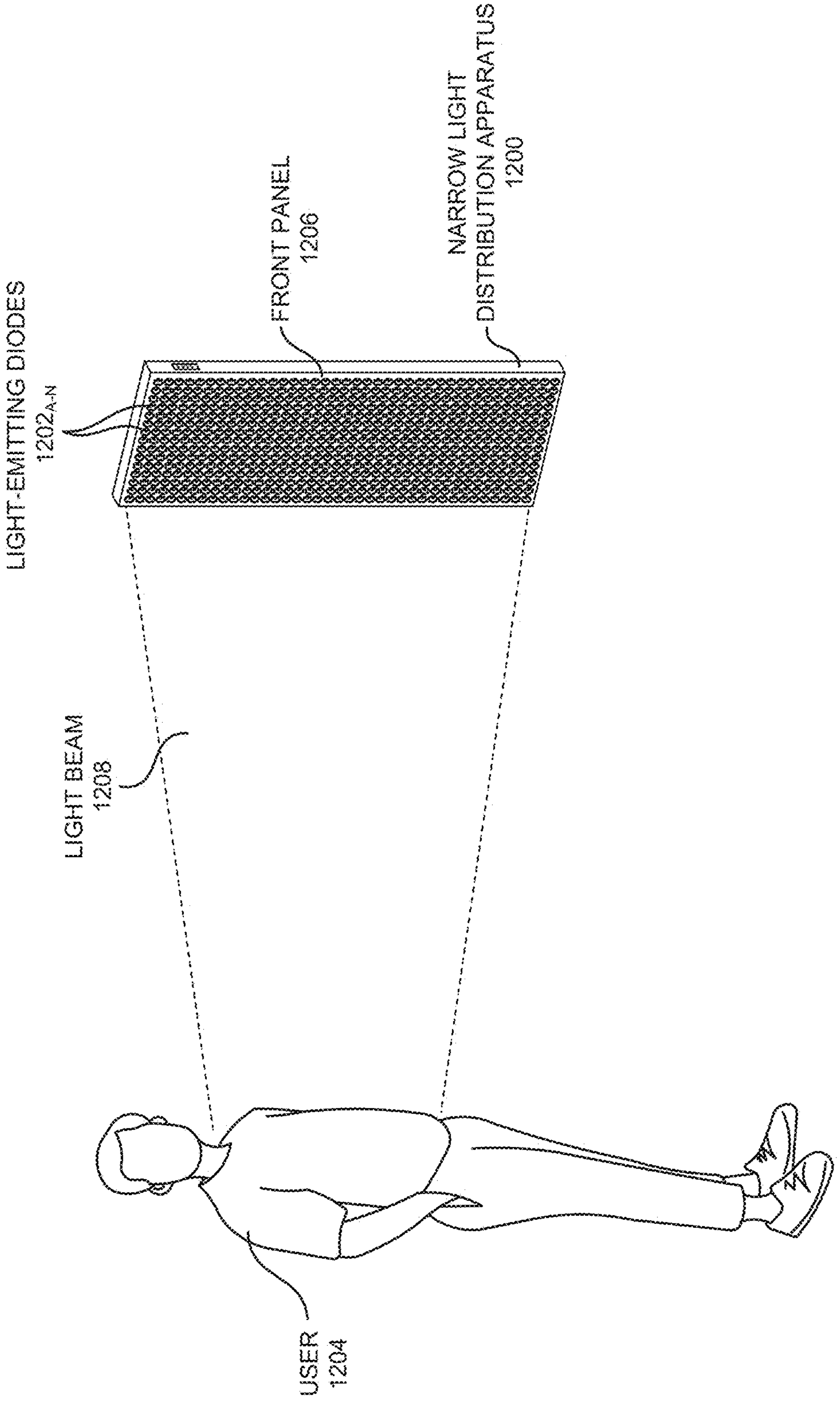
FIG. 12 is a functional view of the narrow light distribution apparatus of FIGS. 6-10, according to one embodiment.

FIG. 12 is a functional view of the narrow light distribution apparatus 100 and/or 600 of FIGS. 1-5 and FIGS. 6-10, according to one embodiment. FIG. 12 shows a narrow light distribution apparatus 1200, a plurality of light-emitting diodes 1202A-N. a user 1204, a front panel 1206, and a light beam 1208 (e.g. the light beam 1108), according to one embodiment.

FIG. 12 shows a user 1204 with their body facing the narrow light distribution apparatus 1200 (e.g. the narrow light distribution apparatus 100 of FIGS. 1-5 and/or the narrow light distribution apparatus 600 of FIGS. 6-10) such that a front panel 1206 (e.g. the front panel 106 and/or the front panel 610) of the narrow light distribution apparatus 1200 is facing the user with a plurality of light-emitting diodes 1202A-N (e.g. the light-emitting diodes 102A-N, the first light-emitting diodes 602A-N, and/or the second light-emitting diodes 604A-N) directed at the user 1204, according to one embodiment. A light beam 1208 may be projected from the plurality of light-emitting diodes 1202A-N toward the user 1204. The light beam 1208 may be projected at any portion of the user 1204 for any period of time, according to one embodiment.

Figure 13:
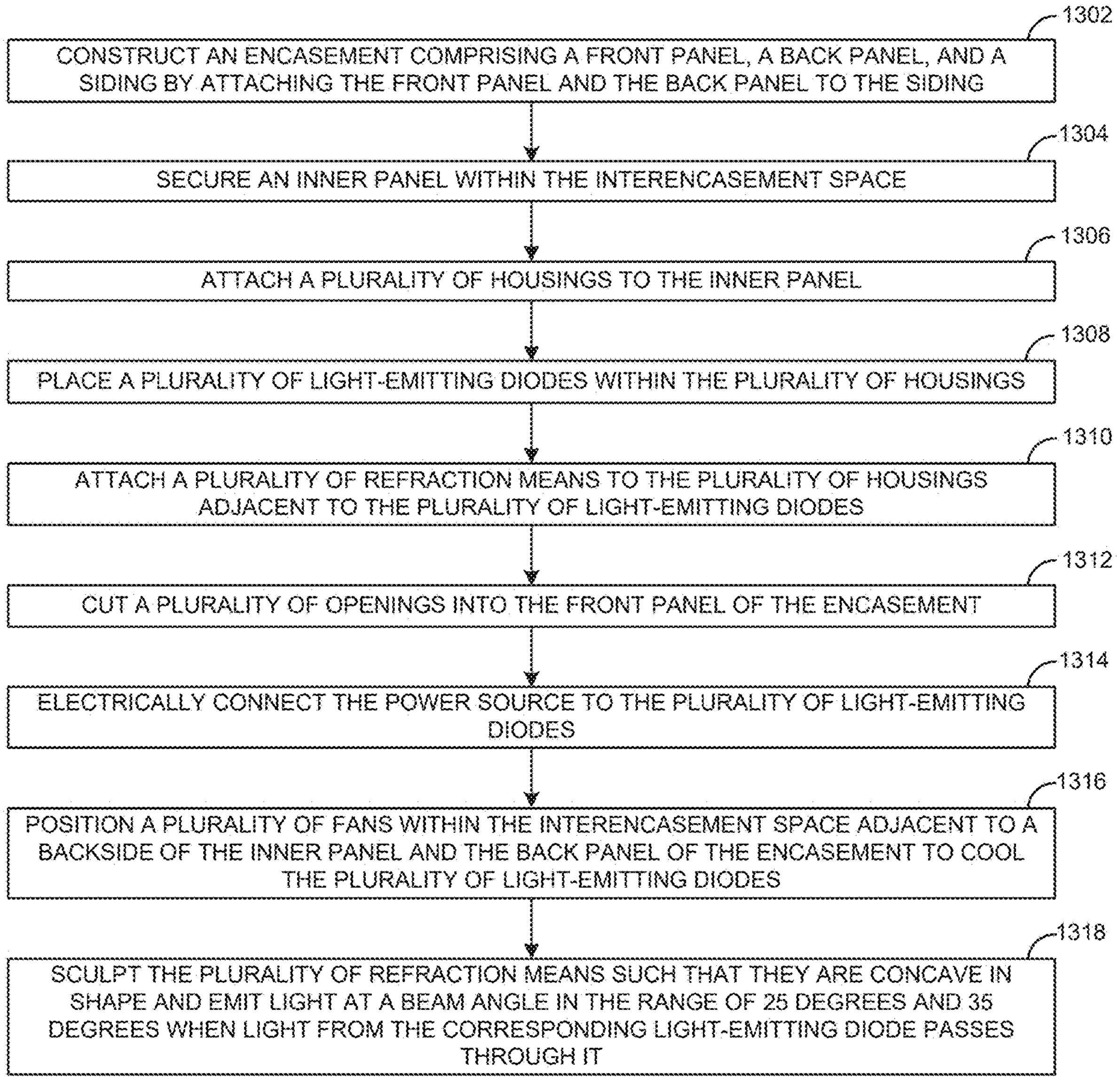
FIG. 13 is a process flow diagram describing the method of forming the narrow light distribution apparatus of FIGS. 1-5 and FIGS. 6-10, according to one embodiment.

FIG. 13 is a process flow diagram describing a method of manufacturing a narrow light distribution apparatus, according to one embodiment. In operation 1302, an encasement comprising a front panel, a back panel, and a siding may be constructed by attaching the front panel and the back panel to the siding. In operation 1304, an inner panel may be secured within the interencasement space. In operation 1306, a plurality of housings may be attached to the inner panel. In operation 1308, a plurality of light-emitting diodes may be placed within the plurality of housings. In operation 1310, a plurality of refraction means may be attached to the plurality of housings adjacent to the plurality of light-emitting diodes. In operation 1312, a plurality of openings may be cut into the front panel of the encasement. In operation 1314, the power source may be electrically connected to the plurality of light-emitting diodes. In operation 1316, a plurality of fans may be positioned within the interencasement space adjacent to a backside of the inner panel and the back panel of the encasement to cool the plurality of light-emitting diodes. In operation 1318, the plurality of refraction means may be sculpted such that they are concave in shape and emit light at a beam angle in the range of 25 degrees and 35 degrees when light from the corresponding light-emitting diode passes through it.

Figure 14:
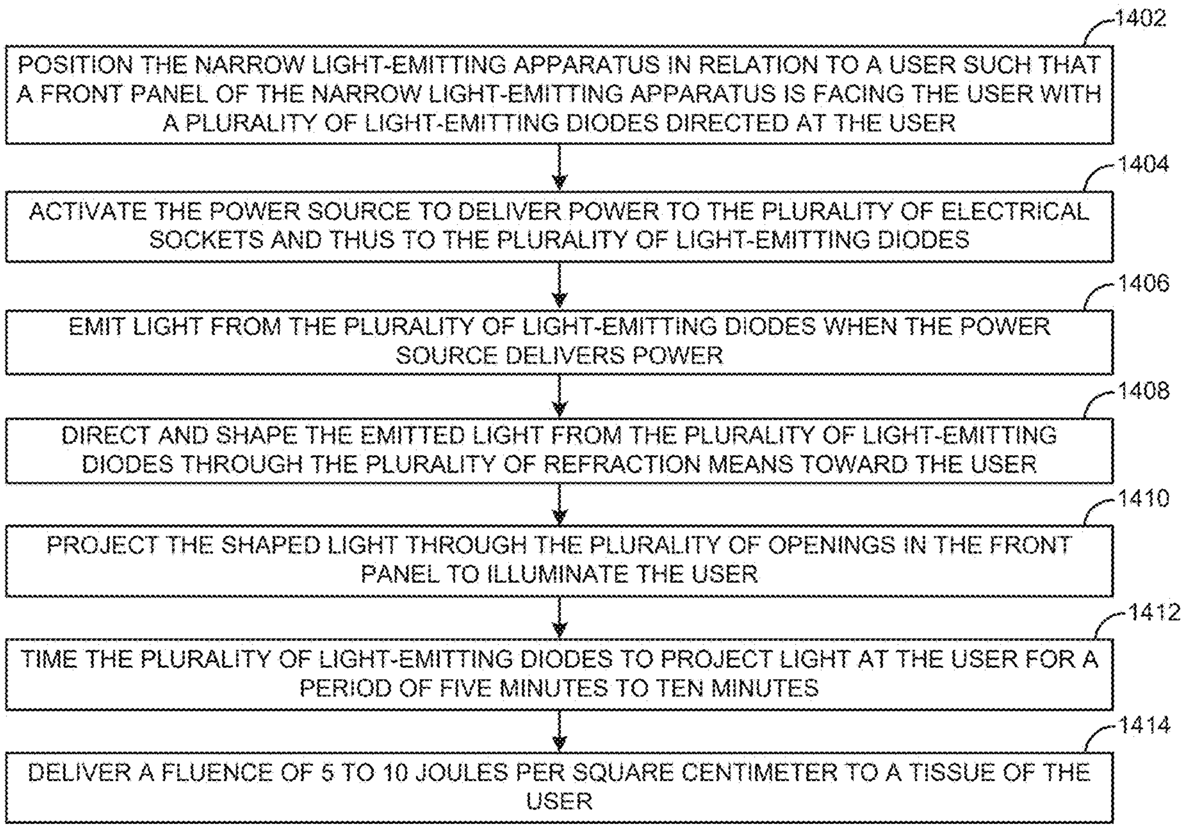
FIG. 14 is a process flow diagram describing the method of using the narrow light distribution apparatus of FIGS. 1-5 and FIGS. 6-10, according to one embodiment.

According to one embodiment, FIG. 14 is a process flow diagram describing a method of using the narrow light distribution apparatus of FIGS. 1-5 and/or FIGS. 6-10. In operation 1402, the narrow light-emitting apparatus may be positioned in relation to a user such that the front panel of the narrow light-emitting apparatus is facing the user with a plurality of light-emitting diodes directed at the user. In operation 1404, the power source may be activated to deliver power to the plurality of electrical sockets and thus to the plurality of light-emitting diodes. In operation 1406, light may be emitted from the plurality of light-emitting diodes when the power source delivers power. In operation 1408, the emitted light from the plurality of light-emitting diodes may be directed and shaped through the plurality of refraction means toward the user. In operation 1410, the shaped light may be projected through the plurality of openings in the front panel to illuminate the user. In operation 1412, the plurality of light-emitting diodes may be timed to project light at the user for a period of five minutes to ten minutes. In operation 1414, a fluence of 5 to 10 joules per square centimeter may be delivered to the tissue of the user.

To achieve effective therapeutic outcomes, the apparatus delivers a specific fluence of light energy to the tissue. The fluence (F) delivered by the apparatus is measured in joules per square centimeter (J/cm$^2$) and is calculated as the product of the intensity (I) of the light and the exposure time (T):

$$\text{Fluence } (F) = \text{Intensity } (I) \times \text{Time } (T)$$

Calculation of Intensity (I):

The intensity of the light (in watts per square centimeter, W/cm$^2$) is determined by the power output (P) of each LED divided by the area (A) over which the light is distributed. The area is calculated based on the distance (D) from the LED to the target tissue and the beam angle (θ):

$$\text{Intensity } (I) = \frac{\text{Power Output } (P)}{\text{Area } (A)}$$

For a given distance (D) and beam angle (θ), the radius (r) of the beam at the target distance can be calculated using the tangent function:

$$r = D \times \tan\left(\frac{\theta}{2}\right)$$

The area (A) of the circular beam is then:

$$A = \pi \times r^2$$

A plain English example will now be described. Jim is a 45-year-old man who is semi-active and of average health, according to one embodiment. He struggles with a persistent muscle injury that causes him significant discomfort and affects his daily activities, according to one embodiment. After trying various treatments with little success, Jim's physician recommends a new, innovative therapy using the MedWave™ Narrow Light™ (e.g. the narrow light distribution apparatus 100 of FIGS. 1-5 and/or the narrow light distribution apparatus 600 of FIGS. 6-10), according to one embodiment.

Jim is curious and eager to try this new apparatus, system, and method, according to one embodiment. He receives detailed instructions on how to use the MMedWave™ Narrow Light™, which is designed to emit focused beams of light to provide targeted therapeutic benefits, according to one embodiment. Jim carefully unboxes the MedWave™ Narrow Light™ and reads through the user manual, according to one embodiment. He notices the device comprises several components, including an encasement with a front panel, back panel, and siding, according to one embodiment. Inside the encasement, there is an inner panel equipped with a grid of electrical sockets, each connected to a housing that holds a light-emitting diode (LED), according to one embodiment.

Jim follows the instructions to position the device correctly, according to one embodiment. He sets it up so that the front panel faces the area of his body he wants to treat, directing the plurality of light-emitting diodes towards his injured muscle, according to one embodiment. The device is to be positioned between six and eight inches away from his body and/or injured body part to ensure optimal results, according to one embodiment.

Once everything is in place, Jim turns on the device by activating the control panel, according to one embodiment. This control panel allows him to adjust various settings, including the light intensity and/or timer, according to one embodiment. He sets the timer for a five-minute session, as recommended by his physician, to ensure a safe and effective treatment duration, according to one embodiment. The LEDs within the apparatus emit light at specific wavelengths for promoting tissue healing and reducing inflammation, according to one embodiment.

As the device powers up, the LEDs begin to emit light through the concave refraction means, which directs and/or shapes the light beams to ensure a focused and consistent distribution, according to one embodiment. Jim feels a gentle warmth on his injured muscle as the light penetrates his skin and reaches the underlying tissues, according to one embodiment. The concave refraction means are designed to produce a beam angle between 25 degrees and 35 degrees, ensuring that the light is precisely targeted to the affected area, according to one embodiment. This targeted approach allows the light energy to penetrate deeply into Jim's tissues, stimulating cellular processes and promoting healing, according to one embodiment.

The focused and sufficiently powered light from the MedWave™ Narrow Light™, with each LED operating at a wattage between four watts and six watts, activates Jim's mitochondria, the energy-producing structures within cells, according to one embodiment. When the mitochondria absorb the light, they increase the production of adenosine triphosphate (ATP), the primary energy carrier in cells, according to one embodiment. This increase in ATP production enhances cellular metabolism and energy availability, crucial for healing and regeneration processes, according to one embodiment.

The power of the light is essential in creating this mitochondrial activation, as it provides the necessary energy to penetrate the tissue and reach the cellular level effectively, according to one embodiment. The intensity and fluence of the light ensure that the mitochondria receive adequate stimulation to boost ATP production, according to one embodiment.

Moreover, the light therapy helps to reduce oxidative stress and inflammation in Jim's injured muscle, according to one embodiment. The light exposure increases the production of reactive oxygen species (ROS) within a controlled range, which in turn activates signaling pathways that promote healing, according to one embodiment. The improved cellular environment facilitates better nutrient delivery and waste removal, aiding the overall recovery of the muscle tissue, according to one embodiment.

Jim follows this treatment regimen daily, using the device for five to ten minutes each session, according to one embodiment. He may rotate the body part and do the treatment again but from a different angle, such as seven minutes at the front of his forearm and seven minutes at the back of his forearm, or until each side receives a fluence of 5 to 10 joules per square centimeter, according to one embodiment. Over the next few weeks, he notices a significant improvement in his muscle injury, according to one embodiment. The pain gradually subsides, and he regains mobility and strength in the affected area, according to one embodiment.

Thanks to the MedWave™ Narrow Light™, Jim experiences a remarkable recovery from his muscle injury, according to one embodiment. The targeted light therapy proves to be an effective and non-invasive treatment, allowing him to return to his normal activities without discomfort, according to one embodiment. Jim is grateful for this advanced technology and the relief it brings to his life, according to one embodiment.

Although the present embodiments have been described with reference to specific example embodiments, it will be evident that various modifications and changes may be made to these embodiments without departing from the broader spirit and scope of the various embodiments.

A number of embodiments have been described. Nevertheless, it will be understood that various modifications may be made without departing from the spirit and scope of the claimed invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

It may be appreciated that the various systems, methods, and apparatus disclosed herein may be embodied in a machine-readable medium and/or a machine accessible medium compatible with a data processing system (e.g., a computer system), and/or may be performed in any order.

The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

The invention claimed is:

1. An apparatus comprising:

an encasement comprising a front panel, a back panel, and a siding, the front panel includes a plurality of openings;

an inner panel positioned within an interencasement space defined by the front panel, back panel, and siding, the inner panel including a plurality of electrical sockets arranged on a front side of the inner panel and electrically connected to a power source, wherein the inter-encasement space is formed within the encasement by attaching the siding to the front panel and the back panel;

a plurality of housings, each housing individually attached to a respective electrical socket and configured to receive electrical power from the electrical socket;

a plurality of light-emitting diodes, each light-emitting diode at least partially within one housing, the plurality of light-emitting diodes including:

first light-emitting diodes that emit light having a wavelength between 600 and 650 nanometers, and second light-emitting diodes that emit light having a wavelength between 800 and 850 nanometers, wherein the first and second light-emitting diodes are arranged in a checkerboard pattern on the inner panel;

a plurality of refraction elements, each refraction elements aligned with one of the plurality of light-emitting diodes to direct light emitted from the light-emitting diodes through a corresponding opening of the front panel away from the inner panel, wherein each refraction element is concave in shape and is at least one of a lens, a prism, a diffraction grating, a holographic optical element, and a fiber optic component, wherein each refraction element directs the light emitted from the light-emitting diode away from the inner panel, and wherein each refraction element produces a beam angle between 25° and 35°;

a plurality of fans positioned between the inner panel and the back panel, and a plurality of air inlets in the back panel positioned adjacent to the fans; and a control panel located on the siding of the encasement to provide an interface to control at least one of an on/off switch, light intensity, a timer, and light pulsing, wherein the control panel provides feedback to a user through at least one of a LED light, a display, and an audible signal.

2. The apparatus of claim 1, wherein the encasement is a substantially cuboid shape with the front panel and the back panels arranged in parallel and separated by a uniform spacing to facilitate airflow between the panels.

3. The apparatus of claim 1, wherein the plurality of light-emitting diodes are arranged in a grid pattern on the inner panel, and wherein each of the plurality of refraction elements is concave in shape and is configured to produce, for its corresponding light-emitting diode, a light beam having the beam angle between 25° and 35° measured relative to a direction perpendicular to the inner-panel surface when light from the light-emitting diode passes through the refraction element.

4. The apparatus of claim 1 wherein each of the plurality of first light-emitting diodes is configured to emit light having a wavelength between 600 nanometers and 650 nanometers and an optical output power between 4 watts and 6 watts, the first light-emitting diodes being arranged in the grid pattern in alternating positions with second light-emitting diodes.

5. The apparatus of claim 1, wherein each of the plurality of refraction elements is configured to bend the light rays emitted from the light-emitting diode inwards towards a central axis by focusing the light rays into a narrower beam.

6. The apparatus of claim 5, wherein the plurality of light-emitting diodes are arranged and configured to deliver a uniform light intensity across a target area.

7. The apparatus of claim 1 wherein each of the plurality of light-emitting diodes has a wattage between four watts and six watts, wherein the light output of each of the plurality of light-emitting diodes correlates with the power consumption of each of the plurality of light-emitting diodes.

8. The apparatus of claim 1 further comprising:

a plurality of fans positioned within the interencasement space between a backside of the inner panel and the back panel to cool the apparatus.

9. The apparatus of claim 8, wherein the back panel includes a plurality of air inlets positioned substantially adjacent to at least one of the plurality of fans.

10. An apparatus comprising, an encasement comprising a front panel, a back panel, and a siding joined together to define an inter-encasement space;

an inner panel situated within the interencasement space between the front panel and back panel, the inner panel having a front side facing the front panel and carrying a plurality of electrical sockets electrically connected to a power source;

a plurality of housings, each housing individually attached to one of the plurality of electrical sockets and configured to receive electrical power through the electrical socket;

a plurality of first light-emitting diodes and a plurality of second light-emitting diodes attached to the inner panel in a checkered pattern, wherein each first light-emitting diode is at least partially disposed within a respective housing, and wherein each second light-emitting diode is at least partially disposed within a respective housing;

a plurality of refraction elements, each aligned with one of the light-emitting diodes and configured to direct and shape light emitted from the corresponding diode away from the inner panel and through the front panel, wherein each refraction element is concave in shape and comprises at least one of a lens, prism, diffraction grating, holographic optical element, or fiber-optic component, and each refraction element produces a beam angle between 25° and 35°; and a plurality of openings formed in the front panel, each opening aligned coaxially with a corresponding housing, light-emitting diode, and refraction element to permit the directed light to exit the encasement;

a plurality of fans installed within the interencasement space of the encasement to dissipate heat generated by the first light-emitting diodes, the plurality of second light-emitting diodes, and other electronic components and a plurality of air inlets in the back panel positioned adjacent to the plurality of fans to aid airflow and cooling effect; and a control panel located on the siding of the encasement configured to control at least one of an on/off switch, light intensity, a timer, and light pulsing.

11. The apparatus of claim 10 wherein the encasement is a substantially cuboid shape with the front panel and the back panels arranged in parallel and separated by a uniform spacing to facilitate airflow between the panels.

12. The apparatus of claim 10, wherein the plurality of light-emitting diodes are arranged in a grid pattern on the inner panel, and wherein each of the plurality of refraction elements is concave in shape and is configured to produce, for its corresponding light-emitting diode, a light beam having the beam angle between 25° and 35° measured relative to a direction perpendicular to the inner-panel surface when light from the light-emitting diode passes through the refraction elements.

13. The apparatus of claim 10 wherein each of the plurality of first light-emitting diodes is configured to emit light having a wavelength between 600 nanometers and 650 nanometers and an optical output power between 4 watts and 6 watts, the first light-emitting diodes being arranged in the grid pattern in alternating positions with second light-emitting diodes.

14. The apparatus of claim 10 wherein each of the plurality of second light-emitting diodes is configured to emit light having a wavelength between 800 nanometers and 850 nanometers and an optical output power between 4 watts and 6 watts, the second light-emitting diodes being arranged in the grid pattern in alternating positions with the first light-emitting diodes.

15. The apparatus of claim 10 wherein, the control panel to provide an interface equipped with a microcontroller for adjusting the settings of the apparatus and control at least one of an on/off switch, light intensity, a timer, and light pulsing, wherein the control panel provides feedback to a user through at least one of a LED light, a display, and an audible signal.

16. The apparatus of claim 10 wherein each of the plurality of first light-emitting diodes and each of the plurality of second light-emitting diodes comprises a wattage between four watts and six watts, wherein the light output of each of the plurality of light-emitting diodes correlates with the power consumption of each of the plurality of light-emitting diodes.

17. The apparatus of claim 10 further comprising:

a plurality of fans positioned within the interencasement space adjacent to a backside of the inner panel and the back panel of the encasement to cool the components within the interencasement space, wherein the plurality of fans positioned within the interencasement space are mounted on an interior side of the back panel and positioned between the back panel and the backside of the inner panel, and each fan oriented to draw ambient air through the back panel and across the back side of the inner panel to cool the apparatus.

18. The apparatus of claim 17 further comprising:

a plurality of air inlets cut into the back panel, wherein each air inlet is positioned substantially adjacent to at least one of the plurality of fans, wherein each of the plurality of air inlets is axially aligned with an intake of a corresponding one of the plurality of fans, and wherein each of the plurality of air inlets is designed with filters to prevent dust and debris from entering the interencasement space.

19. The apparatus of claim 10 wherein the plurality of electrical sockets, the plurality of refraction elements, and the plurality of openings are arranged in a fifteen unit by forty unit configuration, wherein the plurality of electrical sockets, the plurality of refraction elements, and the plurality of openings are arranged in a grid configuration comprising fifteen rows and forty columns, each row and column being evenly spaced to provide uniform light intensity and symmetrical coverage across a target area.

* * * * *